US009045532B2

(12) United States Patent
Broder et al.

(10) Patent No.: US 9,045,532 B2
(45) Date of Patent: Jun. 2, 2015

(54) SOLUBLE FORMS OF HENDRA AND NIPAH VIRUS G GLYCOPROTEIN

(75) Inventors: Christopher C. Broder, Silver Spring, MD (US); Katharine N. Bossart, San Francisco, CA (US)

(73) Assignee: The Henry M. Jackson Foundation for the Advancement of Military Medicine, Inc., Rockville, MD (US)

( * ) Notice: Subject to any disclaimer, the term of this patent is extended or adjusted under 35 U.S.C. 154(b) by 124 days.

(21) Appl. No.: 13/530,922

(22) Filed: Jun. 22, 2012

(65) Prior Publication Data

US 2013/0171132 A1    Jul. 4, 2013

Related U.S. Application Data

(63) Continuation of application No. 11/629,682, filed as application No. PCT/US2005/024022 on Jul. 7, 2005.

(60) Provisional application No. 60/586,843, filed on Jul. 9, 2004.

(51) Int. Cl.

| *C07K 14/115* | (2006.01) |
|---|---|
| *C07K 14/07* | (2006.01) |
| *A01K 39/00* | (2006.01) |
| *C07K 14/005* | (2006.01) |
| *C07K 16/10* | (2006.01) |
| *G01N 33/569* | (2006.01) |
| *G01N 33/68* | (2006.01) |
| *A61K 39/00* | (2006.01) |

(52) U.S. Cl.
CPC .............. *C07K 14/115* (2013.01); *A61K 39/00* (2013.01); *A61K 2039/505* (2013.01); *C07K 14/005* (2013.01); *C12N 2760/18222* (2013.01); *C07K 14/07* (2013.01); *C07K 16/1027* (2013.01); *G01N 33/56983* (2013.01); *G01N 33/6854* (2013.01)

(58) Field of Classification Search
None
See application file for complete search history.

(56) References Cited

U.S. PATENT DOCUMENTS

| 2009/0041772 A1 | 2/2009 | Broder et al. |
| 2013/0171131 A1 | 7/2013 | Broder et al. |

FOREIGN PATENT DOCUMENTS

WO    2007/005244    1/2007

OTHER PUBLICATIONS

Marsh et al. (Current Opinion in Virology. 2012; 2: 242-247).*
Bossart et al. (Science Translational Medicine. 2012; 4 (146): 1-8).*
Broder et al. (Antiviral Research. 2013; 100: 8-13).*
Bossart et al., "Receptor Binding, Fusion Inhibition, and Induction of Cross-Reactive Neutralizing Antibodies by a Soluble G Glycoprotein of Hendra Virus," Journal of Virology, 79(11): 6690-6702 (2005).
Broder C., "Blocking Hendra and Nipah Virus Fusion and Infection", Presentation at the 4th Frederick Workshop on the Cell Biology of Viral Entry; Frederick, Maryland, USA, May 2-5, 2004.
Chua et al., "Nipah virus: a recently emergent deadly *Paramyxovirus*," Science, 288(5470): 1432-1435 (2000).
Eshaghi et al., "Purification of the extra-cellular domain of Nipah virus glycoprotein produced in *Escherichia coli* and possible application in diagnosis," Journal of Biotechnology 116(3): 221-226 (2005).
Guillaume et al., "Nipah Virus: Vaccination and Passive Protection Studies in a Hamster Model," Journal of Virology, 78(2): 834-840 (2004).
Negrete et al., "EphrinB2 is the entry receptor for Nipah virus, an emergent deadly *Paramyxovirus*," Nature, 436: 401-405 (2005).
Parks et al., "Folding and oligomerization properties of a soluble and secreted form of the *Paramyxovirus* hemagglutinin-neuraminidase glycoprotein," Virology, 178(2): 498-508 (1990).
Tamin et al., "Functional properties of the fusion and attachment glycoproteins of Nipah virus," Virology, 296(1): 190-200 (2002).
Tan et al., "Solubility, immunogenicity and physical properties of the nucleocapsid protein of Nipah virus produced in *Escherichia coli*," Journal of Medical Virology, 73(1): 105-112 (2004).
Xiao et al., "Cell biology of virus entry: A review of the 4th International Frederick Meeting," Molecular Membrane Biology, 21(5): 281-287 (2004).
Michalski et al., "The cleavage activation and sites of glycosylation in the fusion protein of Hendra virus," Virus Research, 69(2):83-93 (2000).
Bossart et al., "Membrane Fusion Tropism and Heterotypic Functional Activities of the Nipah Virus and Hendra Virus Envelope Glycoproteins," Journal of Virology, 76(22): 11186-11198 (2002).
Bossart et al., "Functional Expression and Membrane Fusion Tropism of the Envelope Glycoproteins of Hendra Virus," Virology, 290(1): 121-135 (2001).
Harcourt et al., "Molecular characterization of Nipah virus, a newly emergent *Paramyxovirus*," Virology, 271(2):334-349 (2000).
Wang et al., "Expression and characterization of soluble human parainfluenza virus type 1 hemagglutinin-neuraminidase glycoprotein," J. Virological Method, 98(1):53-61 (2001).
Teng et al., "Contribution of the respiratory syncytial virus G glycoprotein and its secreted and membrane-bound forms to virus replication in vitro and in vivo," Virology, 289(2):283-296 (2001).
Malvoisin et al., "Characterization of a secreted form of measles virus haemagglutinin expressed from a vaccinia virus recombinant," The Journal of general virology, 75(Pt 12):3603-3609 (1994).
Wang et al., "Molecular biology of Hendra and Nipah viruses," Microbes and infection, 3(4):279-287 (2001).
Yu et al., "The attachment protein of Hendra virus has high structural similarity but limited primary sequence homology compared with viruses in the genus *Paramyxovirus*," Virology, 251(2):227-233 (1998).
Crennell et al., "Crystal structure of the multifunctional *Paramyxovirus* hemagglutinin-neuraminidase," Nature Structural Biology, 7(11):1068-1074 (2000).
Bowden et al., "Structural basis of Nipah and Hendra virus attachment to their cell-surface receptor ephrin-B2," Nature Structural and Molecular Biology, 15(6):567-572 (2008).
Plemper et al., "Characterization of a Region of the Measles Virus Hemagglutinin Sufficient for Its Dimerization," Journal of Virology, 74(14): 6485-6493 (2000).
Sequence alignment of SEQ ID No. 16 with database PIR__80 Accession No. T08211 of Yu et al., entry date 1999 (from Yu et al., Virology, 251(2):227-233 (1998)).

* cited by examiner

*Primary Examiner* — Shanon A Foley
(74) *Attorney, Agent, or Firm* — Morgan, Lewis & Bockius LLP

(57) ABSTRACT

This invention relates to soluble forms of G glycoprotein from Hendra and Nipah virus. In particular, this invention relates to compositions comprising soluble forms of G glycoprotein from Hendra and Nipah virus and also to diagnostic and therapeutic methods using the soluble forms of G glycoprotein from Hendra and Nipah virus. Further, the invention relates to therapeutic antibodies including neutralizing antibodies, and vaccines for the prevention and treatment of infection by Hendra and Nipah viruses.

7 Claims, 18 Drawing Sheets

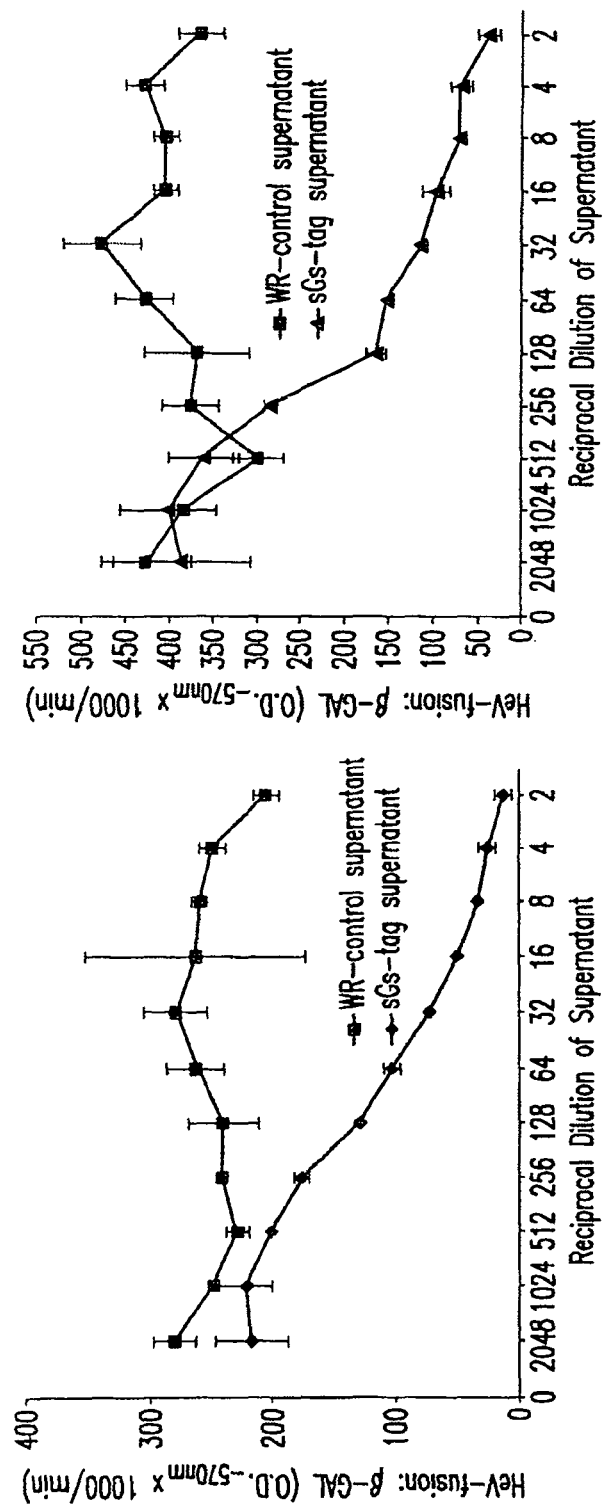

HeV sG$_S$-tag

[diagram: N-term — Ig κ-chain leader sequence / 15 aa linker / S-peptide tag / 15 aa linker — Transmembrane domain/cytoplasmic tail deleted HeV G (aa71–604) — C-term]

HeV sG$_{myc}$-tag

[diagram: N-term — Ig κ-chain leader sequence / 15 aa linker / myc-epitope tag / 15 aa linker — Transmembrane domain/cytoplasmic tail deleted HeV G (aa71–604) — C-term]

Legend:
- Ig κ-chain leader sequence: METDTLLLWVLLLWVPGSTGD (21 aa)
- 15 aa linker: AAQPARRARRTKLGT
- S-peptide tag: KETAAAKFERQHMDS (15 aa)
- myc-epitope tag: EQKLISEEDL (10 aa)
- 15 aa linker: NSADIQHSGGRSTTM

FIG. 6

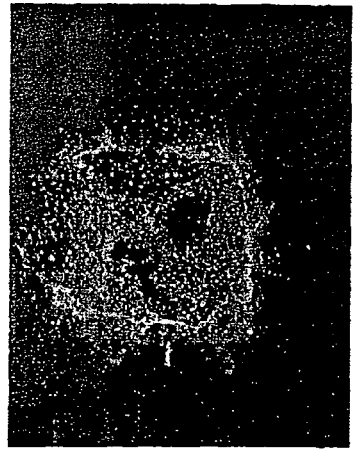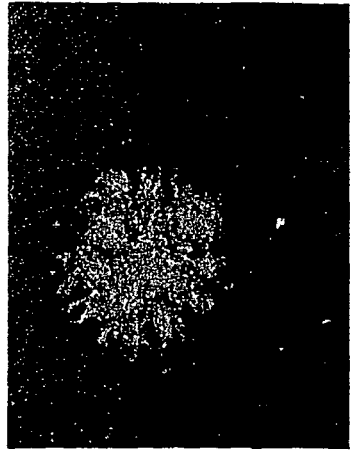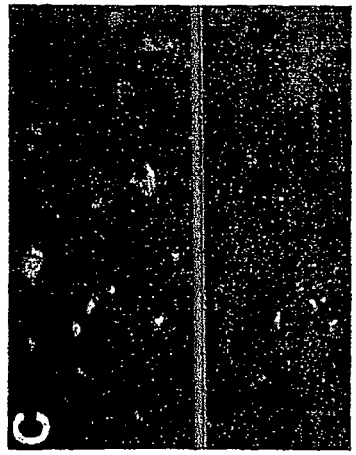

FIG. 11

```
       β6S4                                   β1S1        β1S2
GLPNQICLQK TTSTILKPRL ISYTLPINRE GVCITDPLLA VDNGFFAYSH
RPQ       HE         P
P
183-5     191-5

β1S2             β1S3         β1S4         β2S1
LEKICSCTRG IAKQRIIGVG EVLDRGDKVP SMFMTNVWTP PNPSTIHHCS

β2S1      β2S2          β2S3       β2S4
STYHEDFYYI LCAVSHVGDP ILNSTSWTES SLIPLAVRP KSDSGDYNQK
     Y                                     E
     289                                   324

β3S1          β3S2
YIAITKVERG KYDKVMPYGP SGIKQGDTLY FPAVGFLPRT EFQYNDSNCP

β3S3          β3S4
IIHCKYSKAE NCRLSMGVNS KSHYILRSGL LKYNLSLGGD IILQFIEIAD
DR
385-6

β4S1       β4S2          β4S3  β4S4
NRLTIGSPSK IYNSLGQPVF YQASYSWDTM IKLGDVDT VDPLRVQWRNNS
          F
          447

β5S1       β5S2
VISRPGQSQC PRFNVCPEVC WEGTYNDAFL IDRLNWVSAG VYLNSNQTAE
                              P
                              517

β5S3      β5S4           β6S1       β6S2
NPVFAVFKDN EILYQVPLAE DDTNAQKIII DCFLLENVIW CISLVEIYDI
                                                    K
                                                    570

β6S3
GDSVIRPKLF AVKIPAQCSE S
```

FIG.14

SOLUBLE FORMS OF HENDRA AND NIPAH VIRUS G GLYCOPROTEIN

REFERENCE TO RELATED APPLICATIONS

This application is a continuation application of U.S. application Ser. No. 11/629,682 (filed May 29, 2008) which is a U.S. National Phase Application of International PCT Application PCT/US05/24022 (filed Jul. 7, 2005) which claims the benefit of U.S. Provisional Application 60/586,843 (filed Jul. 9, 2004), all of which are herein incorporated by reference in their entirety.

RIGHTS IN THE INVENTION

This invention was made, in part, with support provided by the United States government under Grant No. U54 AI057168-01, awarded by the National Institute of Allergy and Infectious Diseases, and Grant No. RO731L, awarded by the Uniformed Services University of the Health Sciences, and the United States government may have certain rights in this invention.

SEQUENCE LISTING SUBMISSION VIA EFS-WEB

A computer readable text file, entitled "044508-5022-SubstituteSequenceListing.txt" created on or about Jul. 9, 2014 with a file size of about 17 kb contains the sequence listing for this application and is hereby incorporated by reference in its entirety.

1. FIELD OF THE INVENTION

This present invention relates to soluble forms of a G glycoprotein from Hendra and Nipah virus, to compositions comprising the soluble forms of G glycoprotein from Hendra and Nipah virus, to antibodies reactive against soluble forms of G glycoprotein from Hendra and Nipah virus, and to methods relating thereto.

2. DESCRIPTION OF THE BACKGROUND

Nipah virus and Hendra virus are emerging viruses that are responsible for previously unrecognized fatal diseases in animals and humans. These viruses are closely related members of a new genus, *Henipavirus*, in the Paramyxoviridae family, a diverse group of large, enveloped, negative-sense RNA viruses, that includes a variety of important human and animal pathogens. The recent emergence of these two viruses appears to have been the result of exposure of new hosts precipitated by certain environmental and behavioral changes. Hendra virus was identified first, from cases of severe respiratory disease that fatally affected both horses and man. Subsequent to that appearance, an outbreak of severe febrile encephalitis associated with human deaths occurred in Malaysia. Later studies identified a Hendra-like virus, now known as Nipah virus, as the etiologic agent of that episode. These viruses are unusual among the paramyxoviruses in their abilities to infect and cause disease with high fatality rates in a number of host species, including humans, and are zoonotic Biological Safety Level-4 agents. Presently, the cat appears to be the ideal small-animal model capable of reproducing the pathology seen in infected humans.

Nipah and Hendra virus are NIAID select, category C viruses and possess several features which make them highly adaptable for use as biowarfare agents. For example, both readily grow in cell culture or embryonated chicken eggs, produce high un-concentrated titers near $1\times10^8$ $TCID_{50}$/ml, (14), are highly infectious and transmitted via the respiratory tract (22, 27), and can be amplified and spread in livestock serving as a source for transmission to humans. Recent evidence also indicates that nosocomial transmissibility of NiV from patients with encephalitis to healthcare workers is possible (45, 60).

Fusion of the membrane of enveloped viruses with the plasma membrane of a receptive host cell is a prerequisite for viral entry and infection and an essential step in the life cycle of all enveloped viruses. Research towards dissecting and understanding the mechanisms of this process is an important area of work. Not only does it afford insights into the complex interactions between viral pathogens and their host cells, but it can also shed light on the complex and essential biochemical process of protein-mediated membrane fusion, and also lead to the development of novel intervention and vaccine strategies. This has been demonstrated in the HIV research field, where the discovery of the long-sought coreceptors involved in entry and infection has opened a broad new era in the development of therapeutics to block the infection process at the level of entry (reviewed in (3, 18)).

Paramyxoviruses are negative-sense RNA enveloped viruses and encompass a variety of important human and animal pathogens, including measles virus (MeV), mumps virus, Sendai virus (SeV), Newcastle disease virus (NDV), rinderpest virus, canine distemper virus (CDV), human parainfluenza viruses (hPIV) 1-4, respiratory syncytial virus (RSV), and simian virus 5 (SV5) (reviewed in (36)). In contrast to retroviruses, paramyxoviruses contain two principal membrane-anchored glycoproteins, which appear as spikes projecting from the envelope membrane of the viral particle when viewed under the electron microscope. One glycoprotein is associated with virion attachment to the host cell, and, depending on the particular virus, has been designated as either the hemagglutinin-neuraminidase protein (RN), the hemagglutinin (H), or the G protein which has neither hemagglutinating nor neuraminidase activities (reviewed in (44)). The other glycoprotein is the fusion protein (F) which is directly involved in facilitating the fusion of the viral and host cell membranes (reviewed in (36)). Following virus attachment to a permissive host cell, fusion at neutral pH (or independently of the pH) between the virion and plasma membranes ensues, resulting in delivery of the nucleocapsid into the cytoplasm. In a related process, cells expressing these viral glycoproteins on their surfaces can fuse with receptor-bearing cells, resulting in the formation of multinucleated giant cells (syncytia) under physiological or cell culture conditions.

The Envelope Glycoproteins.

The HN envelope glycoprotein is responsible for attachment of the virion to its receptor, sialic acid, on the target cell as is the case for the hPIVs, NDV, SV5 and others. In contrast, the morbilliviruses, like MeV and CDV, have an attachment protein (H) possessing only hemagglutinating activity and do not bind to sialic acid. MeV was the first morbillivirus shown capable of utilizing a cell-surface protein as a receptor (19, 47), and was the demonstration of the predicted interaction between the MeV H glycoprotein and the MeV receptor CD46 using co-ip experiments and soluble CD46 (48). In addition, MeV field isolates as well as vaccine strains have been shown capable of utilizing signaling lymphocyte activation molecule (SLAM; CD150) (61). SLAM is also capable of serving as a receptor for several other morbilliviruses, including CDV (62).

A third class of paramyxovirus attachment glycoproteins, which are possessed by the Pneumovirinae such as RSV, are designated G, and have neither hemmagglutinating nor neuraminidase activities (reviewed in (44)). The attachment glycoproteins are type II membrane proteins where the molecule's amino (N)-terminus is oriented towards the cytoplasm and the protein's carboxy (C)-terminus is extracellular. The other major envelope glycoprotein is the fusion (F) glycoprotein, and the F of these viruses are more similar, where in all cases it is directly involved in mediating fusion between the virus and host cell at neutral pH.

The F glycoprotein of the paramyxoviruses is a type I integral membrane glycoprotein with the protein's N-terminus being extracellular. It shares several conserved features with other viral fusion proteins, including the envelope glycoprotein (Env) of retroviruses like gp120/gp41 of HIV-1, and hemagglutinin (HA) of influenza virus (reviewed in (26)). The biologically active F protein consists of two disulfide linked subunits, $F_1$ and $F_2$/that are generated by the proteolytic cleavage of a precursor polypeptide known as $F_0$ (reviewed in (34, 55)). Likewise, HIV-1 Env and influenza HA are proteolytically activated by a host cell protease, leading to the generation of a membrane distal subunit analogous to $F_2$ and a membrane-anchored subunit analogous to $F_1$. In all cases, the membrane-anchored subunit contains a new N-terminus that is hydrophobic and highly conserved across virus families and is referred to as the fusion peptide (reviewed in (30)). All paramyxoviruses studied to date require both an attachment and F protein for efficient fusion, with the exception of SV5 which can mediate some fusion in the absence of HN (50). Evidence of a physical association between these glycoproteins has been observed with only limited success and only with NDV (57), hPIV (73), and recently with MeV (51), but these observations have often been with the aid of chemical cross-linking agents. It is hypothesized that following receptor engagement, the attachment protein must somehow signal and induce a conformational change in F leading to virion/cell fusion (35, 53). That conformational distinctions existed in the HN and F of a paramyxovirus depending on whether they were expressed alone or in combination has been noted for quite sometime (13).

The *Paramyxovirus* F envelope glycoproteins, like those of retroviruses, are considered class I membrane fusion-type proteins. An important feature of the fusion glycoproteins of these viruses is the presence of 2 α-helical domains referred to as heptad repeats that are involved in the formation of a trimer-of-hairpins structure during or immediately following fusion (29, 56). These domains are also referred to as either the amino (N)-terminal and the carboxyl (C)-terminal heptad repeats (or HR1 and HR2), and peptides corresponding to either of these domains can inhibit the activity of the viral fusion glycoprotein when present during the fusion process, first noted with sequences derived from the gp41 subunit of HIV-1 envelope glycoprotein (32, 67). Indeed, HIV-1 fusion-inhibiting peptides have met with clinical success and are likely to be the first approved fusion inhibitor therapeutics. Peptide sequences from either the N or C heptads of the F of SV5, MeV, RSV, hPIV, NDV, and SeV have also been shown to be potent inhibitors of fusion (33, 37, 52, 68, 74, 75). It is generally accepted that significant conformational change would occur during activation of paramyxovirus F fusogenic activity. Differential antibody binding reactivities of precursor and proteolytically processed forms of SV5 F (20) and in conjunction with the structure of the post fusion 6-helix bundle of SV5 F (2), strongly support the conformational change model, not only from the pre-fusion to post-fusion structural change, but also from the $F_0$ precursor to the $F_2$-$F_1$ mature protein. That the post-fusion structure of a paramyxovirus F core is likely conserved across other paramyxoviruses has been further supported by the F core structures of RSV (79) and MeV (80). However, recent structural studies on the F glycoprotein of NDV have yielded some different and interesting findings. The oligomeric trimer structure of NDV F (in perhaps the pre-fusion or meta-stable state) has offered some alternative information which distinguishes it from the classic influenza HA structure, this is principally reflected in the completely opposite orientation of the central coiled coils formed by the HR1 (also termed HRA) segments of the trimer (9, 10). To date this is the only structural information on the pre-fusion (or meta-stable) form of a paramyxovirus F (in fact the only other meta-stable, class I, structure other than influenza HA), and perhaps represents a possible third-class of viral fusion proteins.

A precise understanding of how the fusion and attachment glycoproteins function in concert in mediating fusion has yet to be elucidated, but there are two central models proposed for the role of the attachment glycoprotein in the paramyxovirus-mediated membrane fusion process, which were recently detailed by Morrison and colleagues (41), in the context of the HN glycoprotein of NDV. In the first model, the fusion and attachment glycoproteins are not physically associated in the membrane, but following receptor engagement there is an alteration in the attachment glycoprotein which facilitates its association with F and in so doing imparts or facilitates F conformational change leading to membrane fusion. In the second model, the F and attachment glycoprotein are pre-associated and receptor engagement induces conformational alteration in the attachment glycoprotein, and this process alters or releases an interaction with F that allows F to proceed towards its fusion active state—formation of the 6-helix bundle just prior or concomitant with membrane merger. Findings on NDV demonstrate the variable accessibility of the HR1 domain during the process, where HR1 of F are accessible to specific fusion-inhibiting antibody when F is presented in the context of HN, however expression of F alone results in a non-fusogenic version of F with distinctly altered conformation having an HR1 domain which is no longer accessible to antibody (41). The second model is that the attachment glycoprotein is holding F in its non-fusogenic conformation and upon receptor engagement and conformational change in the attachment glycoprotein F is released to undergo conformational changes leading to 6-helix bundle formation and facilitation of membrane fusion. This is supported by observations that paramyxovirus F expressed alone neither mediates fusion (with the exception of SV5 under certain conditions) and has variably antibody accessibility of certain domains such as the NDV F HR1 domain (41). This is perhaps because F alone has transitioned to a fusion triggered or intermediate conformation at an inappropriate moment, which would be consistent with observations of fusion defective or triggered HIV-1 gp41 also referred to as dead-spikes (17). Preliminary findings with HeV and NiV support this second model. Finally, that the attachment glycoprotein of a paramyxovirus undergoes specific conformation alteration when bound to receptor has been recently revealed at the molecular level from studies on the HN glycoprotein of NDV (58, 59). These studies have revealed clear differences in the structure of HN when the receptor-bound glycoprotein is compared to the non-receptor-bound HN structure. In addition, all known viral envelope glycoproteins are homo- or heterooligomers in their mature and functional forms (reviewed in (16)). Multimeric proteins, like these, generally interact over large areas, making structural differences between monomeric subunits and the mature oligomer likely (31). This feature can also translate into differences in antigenic structure and has been shown for a number of proteins, most notably the trimeric influenza HA glycoprotein (69) and HIV-1 gp120/gp41 (7). Indeed, a trimer-specific, potent neutralizing determinant has been mapped to the interface between adjoining subunits of HA, and oligomer-specific anti-HIV-1 Env antibodies have been identified and mapped to conformation-dependent epitopes in gp41 (7). Thus far, all paramyxoviruses, retroviruses, and influenza virus fusion glycoproteins appear to be homotrimers (8, 9, 21, 54, 71), and several HN attachment proteins have been shown to be tetrameric, comprised of a dimer of homodimers. For example, the NDV HN can form dimers and tetramers on the viral surface (40, 43), and recently the crystal structure of the globular head region of the HN dimer from NDV has been solved (15). Finally, and of importance in understanding certain aspects of the immune response to these viruses and the development of vaccines, it is these major envelope glycoproteins of these viruses to which virtually all virus-neutralizing antibodies are directed against.

Emerging Pathogenic Paramyxoviruses.

In 1994, a new paramyxovirus, was isolated from fatal cases of respiratory disease in horses and humans, and was shown to be distantly related to MeV and other members of the morbillivirus genus; it was provisionally termed equine morbillivirus (EMV) but has since been re-named Hendra virus (HeV) (46). The first outbreak of severe respiratory disease in the Brisbane suburb of Hendra Australia resulted in the death of 13 horses and their trainer, and the non-fatal infection of a stable hand and a further 7 horses. At approximately the same time, in an unrelated incident almost 100 km north of Hendra, a 35-year-old man experienced a brief aseptic meningitic illness after caring for and assisting at the necropsies of two horses subsequently shown to have died as a result of HeV infection. Thirteen months later this individual suffered a recurrence of severe encephalitis characterized by uncontrolled focal and generalized epileptic-activity. A variety of studies that were performed in the evaluation of this fatality, including serology, PCR, electron microscopy (EM) and immunohistochemistry, strongly suggested that HeV was indeed the cause of this patient's encephalitis, and the virus was acquired from the HeV-infected horses 13 months earlier (49). In all, fifteen horses and two people died in the two episodes. At the time the source of the emerging virus was undetermined, but more recently it has been found that approximately 50% of certain Australian fruit bat species, commonly known as flying foxes, have antibodies to HeV and Hendra-like viruses have been isolated from bat uterine fluids. It appears that these animals are the natural host for the virus (22, 24, 25, 76). Recently, the nucleic acid sequence of HeV genes has been analyzed and compared with those of other paramyxoviruses (64, 77, 78). These studies have confirmed that HeV is a member of the Paramyxoviridae, subfamily Paramyxovirinae.

Subsequent to these events, an outbreak of severe encephalitis in people with close contact exposure to pigs in Malaysia and Singapore occurred in 1998 (1). The outbreak was first noted in September 1998 and by mid-June 1999, more than 265 cases of encephalitis, including 105 deaths, had been reported in Malaysia, and 11 cases of disease with one death reported in Singapore. This outbreak had a tremendous negative economic impact, which continues to date. Although successful, measures taken in the early days of the outbreak resulted in the slaughter of approximately 1.3 million pigs and the virtual closure of the pig farming industry in peninsular Malaysia. EM, serologic, and genetic studies have since indicated that this virus is also a paramyxovirus, and was closely related to HeV. This virus was named Nipah virus (NiV) after the small town in Malaysia from which the first isolate was obtained from the cerebrospinal fluid of a fatal human case (11, 12, 23, 38, 39).

Most human patients present with acute encephalitis, which in the Malaysia outbreak of 1998-1999 ultimately resulted in a mortality rate of approximately 40%, but infection can also present as a nonencephalitic or asymptomatic episode with seroconversion. Interestingly, infection with NiV can also take a more chronic course with more serious neurological disease occurring late (greater than 10 weeks) following a nonencephalitic or asymptomatic infection. On the other hand, the recurrence of neurological manifestations (relapsed encephalitis) has also been noted in patients who had previously recovered from acute encephalitis. Cases of relapsed-encephalitis presented from several months to nearly two years after the initial infection (72) Taken together, there was nearly a 10% incidence rate of late encephalitic manifestations with a mortality rate of 18%. Thus, with both NiV and HeV a prolonged period of infection is possible before serious neurological disease occurs. The underlying mechanisms which allow these viruses, especially NiV, to escape immunological clearance for such an extended period are completely unknown.

In the case of NiV, the late presentation of neurological disease and IgG subclass response showed similarities to subacute sclerosing panencephalitis (SSPE), a rare late manifestation of MeV infection (72). It was molecular characterization of HeV and NiV which distinguished them as distinctly new paramyxoviruses. The families Paramyxoviridae, Filoviridae, Rhabdoviridae, and Bornaviridae are all negative-sense RNA enveloped viruses sharing similar genome organization, replication strategies, and polymerase domain structure (63). These families are grouped in the order Mononegavirales, the first taxon above family level virus taxonomy. The genome size in the Mononegavirales is wide ranging, ~8.9-19.1 kb. The genomes of paramyxoviruses, as a group, are generally considered tightly spread, having sizes in the range of 15.1-15.9 kb, except HeV and NiV whose genomes of 18.2 kb, far closer in size to the Filoviridae. Much of this added length is untranslated regions at the 3' end in the six transcription units, again quite similar to Marburg and Ebloa Filoviruses (63). Also, the P protein is larger by 100 residues (longest known), and a small basic protein (SB) in HeV of unknown function. Taken together, the molecular features of both HeV and NiV make them unusual paramyxoviruses, as does their ability to cause potentially fatal disease in a number of species, including humans.

Pathogenesis.

The development or characterization of animal models to study these newly identified viral zoonoses is important for understanding their pathogenic features and in the development of therapeutics. Of the two fatal cases of HeV infection in humans, the first was the result of severe respiratory disease following several days of ventilated life-support. The patient's lungs had gross lesions of congestion, hemorrhage and oedema associated with histological chronic alveolitis with syncytia. The second fatal case was one of leptomeningitis with lymphocytes and plasma cells and foci of necrosis in various parts of the brain parenchyma, after initial infection more than 1 year previously (reviewed in (27)). Multinucleate endothelial cells were also seen in the viscera as well as in the brain. In contrast, there were many more human cases of infection with NiV. More than 30 individuals resulting from the large NiV outbreak in Malaysia and Singapore were autopsied, and the immuno- and histological features included systemic endothelial infection accompanied by vasculitis, thrombosis, ischaemia and necrosis (reviewed in (27)). These changes were especially noted in the central nervous system (CNS). Immunohistochemical analysis have also shown widespread presence of NiV antigens in neurons and other parenchymal cells in necrotic foci seen in the CNS as well as in endothelial cells and media of affected vessels (27). In infected humans, evidence of vasculitis and endothelial infection was also seen in most organs examined. Disseminated endothelial cell infection, vasculitis, and CNS parenchymal cell infection play an essential role in the fatal outcome of NiV infection in humans (reviewed in (27)). The principal zoonotic episodes in nature involved the horse in the HeV cases and the pig in the case of NiV. Both these viruses have a notable broad host cell tropism in in vitro studies (4, 5). These observations correlated to what has been observed in natural and experimental infection.

Experimental infections of the horse and pig have been carried out with HeV and NiV respectively and one naturally NiV-infected horse has been examined. The pathology caused by either virus in horses appears to be more severe than that caused by NiV in pigs. In addition to pigs, HeV infection of cats has also been performed and in this case disease resembles that seen in horses, characterized by generalized vascular disease with the most severe effects seen in the lung (28). Guinea pigs have also been experimentally infected with HeV (28) and the pathology seen differed significantly in several respects in comparison to the human cases as well as natural and experimentally infected horses. In guinea pigs HeV caused generalized vascular disease but, unlike horses and cats, there was little or no pulmonary oedema. Histologically, vascular disease was prominent in arteries and veins, and in many organs such as the lung, kidney, spleen, lymph nodes, gastrointestinal tract and skeletal and intercostal muscles. NiV infection of the guinea pig has not yet been well described.

In regards to other small laboratory animal models, NiV and HeV do not cause disease in mice even after subcutaneous administration, however, and not surprisingly, they will kill mice if administered intracranially. Further, there is also no serological evidence for NiV in rodents in Malaysia, and several hundred sera were tested during the outbreak. Evidence of natural NiV infections were also noted in dogs and cats.

In experimental NiV infection of the cat, gross lesions in animals with severe clinical signs strongly resembled those of cats infected with HeV. These consisted of hydrothorax, oedema in the lungs and pulmonary lymph nodes, froth in the bronchi, and dense purple-red consolidation in the lung. There were also similar features in the histological appearance, diffuse perivascular, peribronchial and alveolar hemorrhage and oedema, vasculitis affecting arteries and arterioles, alveolitis, syncytium formation within endothelial cells and alveolar epithelial cells (reviewed in (27)). Taken together, the evidence to date indicates that the cat represents an animal model whereby the pathology seen most closely resembles the lethal human disease course. In addition, infection of cats with either NiV or HeV is uniformly fatal. NiV and HeV appear to cause similar diseases but with some notable variations, and although the basic pathologic processes have been well described, less is known about the factors which clearly influence disease course depending on the species infected. This is a special concern in human infections, where there is a remarkable ability of these viruses to persist in the host (up to 2 yrs) before causing a recurrence of severe and often fatal disease. Cats succumb within 6-8 days to subcutaneous infection with 5,000, and subcutaneous or oral administration of 50,000, $TCID_{50}$ of a low passage, purified HeV (65, 66, 70). Experimental infection of cats with NiV has confirmed the susceptibility of this species to oronasal infection with 50,000 $TCID_{50}$ NiV (42). In summary, the clinical and pathological syndrome induced by NiV in cats was comparable with that associated with HeV infection in this species, except that in fatal infection with NiV there was extensive inflammation of the respiratory epithelium, associated with the presence of viral antigen.

In summary, recurrent outbreaks of NiV resulting in significant numbers of human fatalities have recently been confirmed (Fatal fruit bat virus sparks epidemics in southern Asia. Nature 429, 7, 06 May 2004). HeV is also know to cause fatalities in human and animals and is genetically and immunologically closely related to NiV. There are presently no vaccines or therapeutics for prevention of infection or disease caused by Nipah virus or Hendra virus. Both Nipah virus and Hendra virus are United States, National Institute of Allergy and Infectious Disease, category C priority agents of biodefense concern. Further, as these viruses are zoonotic Biological Safety Level-4 agents (BSL-4), production of vaccines and/or diagnostics, with safety is very costly and difficult. Thus, there is a need for a Nipah virus or Hendra virus vaccines and diagnostics that allow for high throughput production of vaccines and/or diagnostics. All references cited herein, including patent applications and publications, are incorporated by reference in their entirety.

SUMMARY OF THE INVENTION

The present invention overcomes the problems and disadvantages associated with current strategies and designs and provides new tools and methods for the design, production and use of soluble forms of the G envelope glycoprotein of Hendra virus and Nipah virus.

One embodiment of the invention is directed to polynucleotides and polypeptides or fragments thereof encoding a soluble G protein derived from Hendra virus.

Another embodiment of the invention is directed to polynucleotides or polypetides or fragments thereof encoding a soluble G protein derived from Nipah virus.

Another embodiment is directed to methods of producing soluble G protein derived from Hendra virus and/or Nipah virus.

Another embodiment is directed to expression vectors comprising the polynucleotides encoding a soluble G protein derived from Hendra and/or Nipah virus.

Another embodiment is directed to a fusion protein comprising a polypeptide of the invention and one or more other polypetides that enhance the stability of a polypeptide of the invention, enhance the immunogenicity of a polypeptide of the present invention and/or assist in the purification of a polypeptide of the present invention.

Another embodiment is directed to antibodies and fragments thereof, such as neutralizing antibodies, specific for a soluble G protein derived from Hendra and/or Nipah virus and diagnostic and/or therapeutic application of such antibodies.

Another embodiment is directed to subunit vaccine comprising the polynucleotides or polypeptides of the invention.

Another embodiment of the invention is directed to methods of preventing infection with Hendra and/or Nipah virus in a subject or mitigating an infection of Hendra and/or Nipah virus in a subject.

Another embodiment of this invention is directed to diagnostic kits comprising the polynucleotides, polypeptides and/or antibodies of the invention.

Other embodiments and advantages of the invention are set forth in part in the description, which follows, and in part, may be obvious from this description, or may be learned from the practice of the invention.

DESCRIPTION OF THE FIGURES AND TABLE

FIG. 1 shows expression of soluble HeV G envelope glycoprotein. Vaccinia virus encoding either a myc-tag or S-tag soluble HeV G was produced by metabolic labeling in HeLa cells. Control is wild-type HeV G. Specific precipitation of each sG construct is shown by precipitation from either lysates or supernatants using myc MAb or S-beads.

FIG. 2 shows inhibition of HeV and NiV-mediated fusion by sG S-tag. HeLa cells were infected with vaccinia recombinants encoding HeV F and HeV G or NiV F and NiV G glycoproteins, along with a vaccinia recombinant encoding T7 RNA polymerase (effector cells). Each designated target cell type was infected with the *E. coli* LacZ-encoding reporter vaccinia virus vCB21R. Each target cell type ($1\times10^5$) was plated in duplicate wells of a 96-well plate. sG S-tag or control supernatants were added and incubated for 30 minutes at 37° C. The HeV or NiV glycoprotein-expressing cells ($1\times10^5$) were then mixed with each target cell type. After 2.5 hr at 37° C., Nonidet P-40 was added and β-Gal activity was quantified. Panels A and B: Inhibition of HeV-mediated fusion by sG S-tag-infected supernatant or WR-infected supernatant in U373 cells (Panel A) or PCI 13 cells (Panel B). Panels C and D: Inhibition of HeV and NiV-mediated fusion by sG S-tag in U373 cells (Panel C) or PCI 13 cells (Panel D). Panels E and F: Inhibition of HeV- and NiV-mediated fusion by purified sG myc-tag in U373 cells (Panel E) or PCI 31 cells (Panel F).

FIG. 3 shows indirect immunofluorescence of permissive and non-permissive cell lines stained with sHeV G envelope glycoprotein. Cells were plated into 8 well Lab-Tek II chamber slides in the appropriate medium and incubated for 3 days. The cells were fixed with acetone for 2 minutes. HeLa cells represent a fusion non-permissive cell line whereas U373, PCI 13, and Vero represent fusion permissive cell lines. The cells were stained with sG S-tag followed by an anti-HeV G specific rabbit antiserum and a donkey anti-rabbit Alexa Fluor 488 conjugate. Samples were examined with an Olympus microscope with a reflected light fluorescence attachment and an Olympus U-M41001 filter. All images were obtained with a SPOT RT CCD digital camera at an original magnification of 40×. Panel A: sG S-tag and donkey anti-rabbit Alexa Fluor 488 conjugate. Panel B: sG S-tag, anti-HeV G antiserum, and donkey anti-rabbit Alexa Fluor 488 conjugate.

FIG. 4 shows expression of soluble NiV G envelope glycoprotein. Vaccinia virus encoding S-tag soluble HeV G, or plasmid expression vectors encoding S-tag soluble HeV G or NiV G were produced by metabolic labeling in HeLa cells. Specific precipitation of each sG construct is shown by precipitation from either lysates or supernatants using S-beads.

FIG. 5 shows analysis of the oligomeric structures of soluble HeV G envelope glycoprotein. HeLa cells were infected with sHeV G (S-tag) encoding vaccinia virus and incubated 16 h at 37° C. (4 wells of a 6 well plate). Beginning at 6 h post-infection, the cells were metabolically labeled overnight with [35S]-met/cys. Supernatants were removed, clarified by centrifugation, concentrated, buffer exchanged into PBS. One half (400 μl) of the sHeV G was then cross-linked with DTSSP [3,3'-Dithiobis(sulfosuccinimidylpropionate)] (4 mM/RT°/15 min) quenched with 100 mM Tris pH 7.5. The cross-linked and un-cross linked preparations were then divided into two equal portions and layered onto continuous (5-20%) sucrose gradients (4 gradients) and fractioned. All fractions were then precipitated with S-protein agarose, and the samples of metabolically labeled sG were resolved by 10% SDS-PAGE under reducing and non-reducing conditions and detected by autoradiography.

FIG. 6 shows a schematic of soluble Hey G glycoprotein constructs. IgK-chain linker (SEQ ID NO. 10); 15 aa linker (SEQ ID NO. 11); S-peptide tag (SEQ ID NO. 12); c-myc-epitope tag (SEQ ID NO 13); 15 aa linker (SEQ ID NO. 14).

FIG. 7 shows a molecular weight profile of HeV sG. A panel of high molecular weight standards was separated on a Superdex 200 size exclusion column and a calibration curve was generated. Samples of purified $sG_{S\text{-}tag}$ and $sG_{myc\text{-}tag}$ were separated on the calibrated Superdex 200 column and fractionated. The Kay values of major sG peaks were calculated and their apparent molecular weights were determined using the calibration curve from the molecular weight standards. The figure shows the three principal peaks observed with $sG_{S\text{-}tag}$. The molecular estimates shown associated with each of the three peaks (peak 1, 2 and 3) are the averages of seven independent separations of three different $sG_{S\text{-}tag}$ preparations.

FIG. 8 shows oligomeric forms of $sG_{S\text{-}tag}$. HeLa cells were infected with $sG_{S\text{-}tag}$ encoding vaccinia virus and incubated 16 h at 37° C. Beginning at 6 h post-infection, the cells were metabolically labeled overnight with {35S}-methionine/cysteine. Supernatants were removed, clarified by centrifugation, concentrated, buffer exchanged into PBS. One half (200 μl) of the $sG_{S\text{-}tag}$ was then cross-linked with DTSSP [3,3'-Dithiobis(sulfosuccinimidylpropionate)] (4 mM/RT°/30 min) quenched with 100 mM Tris pH 7.5. The cross-linked and un-cross linked preparations were layered onto continuous (5-20%) sucrose gradients (2 gradients) and fractioned. All fractions were split into 2 tubes (for reducing and non-reducing conditions), fractions were then precipitated with S-protein agarose, and the samples of metabolically labeled sG were resolved by 7.5% SDS-PAGE under reducing and non-reducing conditions and detected by autoradiography. Bottom and top of gradients are indicated. A: non-cross-linked and unreduced, B: non-cross-linked and reduced, C: cross-linked and unreduced, D: cross-linked and reduced.

FIG. 9 shows the oligomeric form of full length HeV G. HeLa cells were infected with HeV G encoding vaccinia virus and incubated 16 h at 37° C. Beginning at 6 h post-infection, the cells were metabolically labeled overnight with {$^{35}$S}-methionine/cysteine. Supernatants were removed and cells were chased for 2 h in complete medium, washed twice in PBS and recovered. The non-cross-linked HeV G-expressing cells were lysed in Triton-X containing buffer, clarified by centrifugation, and layered onto a continuous sucrose gradient (5-20%) and fractioned. All fractions were split into 2 tubes (for reducing and non-reducing conditions), fractions were then precipitated with anti-HeV antiserum followed by Protein G-Sepharose, and the samples of metabolically labeled HeV G were resolved by 7.5% SDS-PAGE under reducing and non-reducing conditions and detected by autoradiography. Bottom and top of gradients are indicated. A: non-cross-linked and unreduced, B: non-cross-linked and reduced.

FIGS. 10 A, B, C and D shows immunofluorescence-based syncytia assay of HeV and NiV. Vero cells were plated into 96 well plates and grown to 90% confluence. Cells were pretreated with $sG_{S\text{-}tag}$ for 30 min at 37° C. prior to infection with $1.5\times10^3$ $TCID_{50}$/ml and $7.5\times10^2$ $TCID_{50}$/ml of live HeV or NiV (combined with $sG_{S\text{-}tag}$). Cells were incubated for 24 hours, fixed in methanol and immunofluorescently labeled for P protein prior to digital microscopy. Images were obtained using an Olympus IX71 inverted microscope coupled to an Olympus DP70 high resolution color camera and all images were obtained at an original magnification of 85×. Representative images of FITC immunofluorescence of anti-P labeled HeV and NR. FIG. 10A: untreated control infections, FIG. 10B: infections in the presence of 100 μg/ml $sG_{S\text{-}tag}$.

FIG. 11 shows inhibition of HeV and NiV infection by $sG_{S\text{-}tag}$. Vero cells were plated into 96 well plates and grown to 90% confluence. Cells were pretreated with $sG_{S\text{-}tag}$ for 30 min at 37° C. prior to infection with $1.5 \times 10^3$ $TCID_{50}$/ml and $7.5 \times 10^2$ $TCID_{50}$/ml of live HeV or NiV (combined with $sG_{S\text{-}tag}$). Cells were incubated for 24 hours, fixed in methanol and immunofluorescently labeled for P protein prior to digital microscopy and image analysis to determine the relative area of each syncytium. Figure shows the relative syncytial area (pixel$^2$) versus $sG_{S\text{-}tag}$ concentration for HeV (circles) and NiV (triangles).

FIG. 14 shows the amino acid sequence of the sG protein (SEQ ID NO 15).

Figure 1:
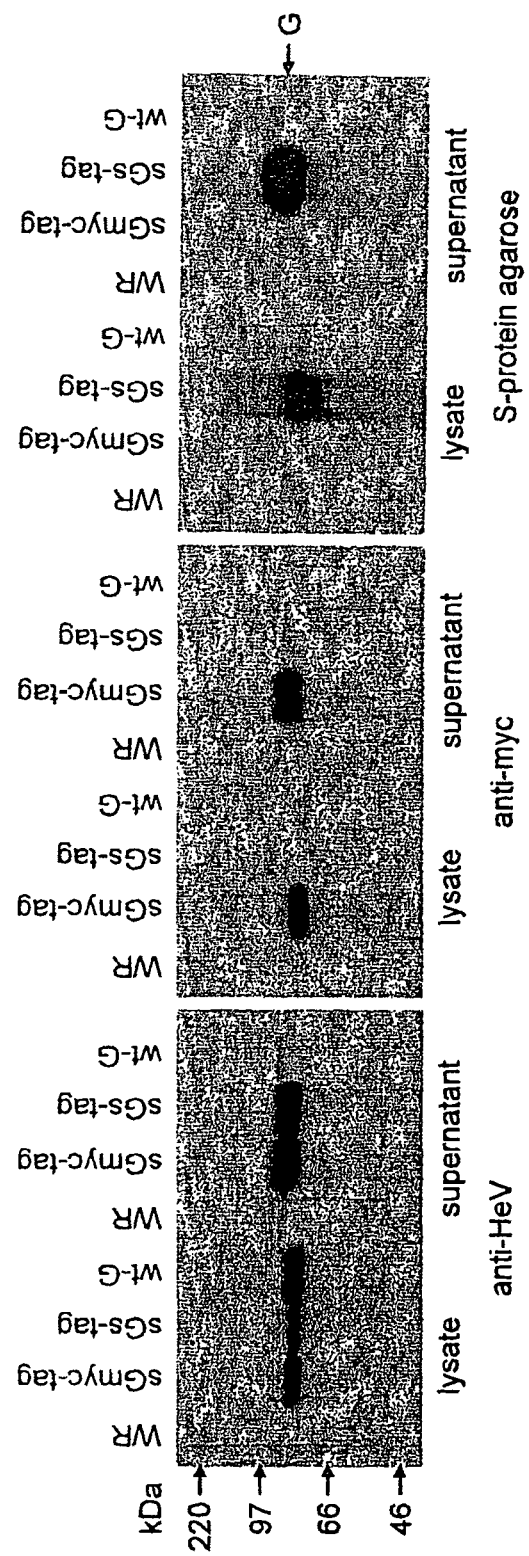

Table 1 shows neutralization of HeV and NiV infection. Anti-HeV G antisera were generated in rabbits by 3 inoculations with purified $sG_{S\text{-}tag}$. Sera collected 2 weeks after the third injection were analyzed in a virus-neutralization assay against HeV and NiV. Serum neutralization titers were determined by presence of CPE (indicated by +) and recorded as the serum dilution where at least one of the duplicate wells showed no CPE.

DESCRIPTION OF THE INVENTION

General Techniques

The practice of the present invention employs, unless otherwise indicated, conventional techniques of molecular biology (including recombinant techniques), microbiology, cell biology, biochemistry and immunology, which are within the skill of the art. Such techniques are explained fully in the literature, such as, for example, *Molecular Cloning: A Laboratory Manual*, second edition (Sambrook, et al., 1989) Cold Spring Harbor Press; *Oligonucleotide Synthesis* (M. J. Gait, ed., 1984); *Methods in Molecular Biology*, Humana Press; *Cell Biology: A Laboratory Notebook* (J. E. Cellis, ed., 1998) Academic Press; *Animal Cell Culture* (R. I. Freshney, ed., 1987); *Introduction to Cell and Tissue Culture* (J. P. Mather and P. E. Roberts, 1998) Plenum Press; *Cell and Tissue Culture: Laboratory Procedures* (A. Doyle, J. B. Griffiths, and D. G. Newell, eds., 1993-8) J. Wiley and Sons; *Methods in Enzymology* (Academic Press, Inc.); *Handbook of Experimental Immunology* (D. M. Weir and C. C. Blackwell, eds.); *Gene Transfer Vectors for Mammalian Cells* (J. M. Miller and M. P. Calos, eds., 1987); *Current Protocols in Molecular Biology* (F. M. Ausubel, et al., eds., 1987); *PCR: The Polymerase Chain Reaction*, (Mullis, et al., eds., 1994); *Current Protocols in Immunology* (J. E. Coligan et al., eds., 1991); *Short Protocols in Molecular Biology* (Wiley and Sons, 1999); *Immunobiology* (C. A. Janeway and P. Travers, 1997); *Antibodies* (P. Finch, 1997); *Antibodies: a practical approach* (D. Catty., ed., IRL Press, 1988-1989); *Monoclonal antibodies: a practical approach* (P. Shepherd and C. Dean, eds., Oxford University Press, 2000); *Using antibodies: a laboratory manual* (E. Harlow and D. Lane (Cold Spring Harbor Laboratory Press, 1999); *The Antibodies* (M. Zanetti and J. D. Capra, eds., Harwood Academic Publishers, 1995).

As used herein, the singular form "a", "an", and "the" includes plural references unless indicated otherwise. For example, "a" G glycoprotein includes one or more G glycoproteins.

Generally this invention provides soluble forms of HeV and NiV G glycoprotein envelope protein, the polynucleotides encoding the proteins and to methods for using these proteins in diagnosis, detection and treatment. Specifically this invention provides soluble forms of HeV and NiV G glycoprotein envelope proteins which retain characteristics of the native viral G glycoprotein allowing for rapid high throughput production of vaccines, diagnostics and screening.

Generally, the soluble forms of the HeV and NiV G glycoproteins comprise all or part of the ectodomain (e.g. extracellular) of the G glycoprotein of a HeV or NiV and are generally produced by deleting all or part of the transmembrane domain of the G glycoprotein and all or part of the cytoplasmic tail of the G glycoprotein. By way of example, a soluble G glycoprotein may comprise the complete ectodomain of an HeV or NiV G glycoprotein. Also by way of example, and not limitation a soluble G glycoprotein may comprise all or part of the ectodomain and part of the transmembrane domain of an HeV or NiV G glycoprotein.

The soluble HeV or NiV G glycoproteins of the invention, generally retain one or more characteristics of the corresponding native viral glycoprotein, such as, ability to interact or bind the viral host cell receptor, can be produced in oligomeric form or forms, or the ability to elicit antibodies (including, but not limited to, viral neutralizing antibodies) capable of recognizing native G glycoprotein. Examples of additional characteristics include, but are not limited to, the ability to block or prevent infection of a host cell. Conventional methodology may be utilized to evaluate soluble HeV or NiV G glycoproteins for one of more of the characteristics. Examples of methodology that may be used include, but are not limited to, the assays described herein in the Examples.

Polynucleotides

The term polynucleotide is used broadly and refers to polymeric nucleotides of any length (e.g., oligonucleotides, genes, small inhibiting RNA, fragments of polynucleotides encoding a protein etc). By way of example, the polynucleotides of the invention may comprise all or part of the ectodomain or all or part of the ectodomain and part of the transmembrane domain. The polynucleotide of the invention may be, for example, linear, circular, supercoiled, single stranded, double stranded, branched, partially double stranded or single stranded. The nucleotides comprising the polynucleotide may be naturally occurring nucleotides or modified nucleotides. Generally the polynucleotides of the invention encode for all or part of the ectodomain (e.g. extracellular) of the G glycoprotein of a HeV or NiV.

Non-limiting examples of sequences that may be used to construct a soluble HeV G glycoprotein can be found in Wang, L. F. et al., *J. Virol.* 74 (21), 9972-9979 (2000) and Yu, M. et al., *Virology* 251 (2), 227-233 (1998) (herein incorporated by reference in their entirety). Non-limiting examples of sequences that may be used to construct a soluble NiV G glycoprotein can be found in Harcourt, B H et al., *Virology* 271: 334-349, 2000 and Chua, K. B. et al, *Science* 288 (5470), 1432-1 (herein incorporated by reference in their entirety). Generally, G glycoprotein sequences from any Hendra virus and Nipah virus isolate or strain may be utilized to derive the polynucleotides and polypeptides of the invention.

By way of example, and not limitation, a polynucleotide encoding a soluble HeV G Glycoprotein may comprise a polynucleotide sequence encoding about amino acids 71-604 of the amino acid sequence for an HeV G Glycoprotein in Wang, L. F. et al., J. Virol. 74 (21), 9972-9979 (2000) (SEQ ID NO: 16) (see also, e.g., Yu, M. et al., Virology 251 (2), 227-233 (1998)). Also by way of example, and not limitation, a polynucleotide encoding a soluble HeV G glycoprotein may comprise nucleotides 9048 to 10727 of the polynucleotide sequence for an HeV G glycoprotein in Wang, L. F. et al., J. Virol. 74 (21), 9972-9979 (2000) (see also, e.g., Yu, M. et al., Virology 251 (2), 227-233 (1998)).

By way of example, and not limitation, a polynucleotide encoding a soluble NiV G glycoprotein may comprise a polynucleotide sequence encoding about amino acids 71-602 of the amino acid sequence for an NiV G Glycoprotein in Harcourt, B H et al., Virology 271: 334-349, 2000 (SEQ ID NO: 17) (see also Chua, K. B. et al., Science 288 (5470), 1432-1). Also by way of example, and not limitation, a polynucleotide encoding a soluble NiV G glycoprotein may comprise nucleotides 9026 to 10696 of the polynucleotide sequence for an HeV G glycoprotein in Harcourt, B H et al., Virology 271: 334-349, 2000 (see also Chua, K. B. et al., Science 288 (5470), 1432-1).

Functional equivalents of these polynucleotides are also intended to be encompassed by this invention. By way of example and not limitation functionally equivalent polynucleotides encode a soluble G glycoprotein of a HeV or NiV and possess one or more of the following characteristics: ability to interact or bind the viral host cell receptor, can be produced in oligomeric form or forms, the ability to elicit antibodies (including, but not limited to, viral neutralizing antibodies) capable of recognizing native G glycoprotein and/or the ability to block or prevent infection of a host cell.

Polynucleotide sequences that are functionally equivalent may also be identified by methods known in the art. A variety of sequence alignment software programs are available in the art to facilitate determination of homology or equivalence. Non-limiting examples of these programs are BLAST family programs including BLASTN, BLASTP, BLASTX, TBLASTN, and TBLASTX (BLAST is available from the worldwide web at ncbi.nlm.nih.gov/BLAST/), FastA, Compare, DotPlot, BestFit, GAP, FrameAlign, ClustalW, and PileUp. These programs are obtained commercially available in a comprehensive package of sequence analysis software such as GCG Inc.'s Wisconsin Package. Other similar analysis and alignment programs can be purchased from various providers such as DNA Star's MegAlign, or the alignment programs in GeneJockey. Alternatively, sequence analysis and alignment programs can be accessed through the world wide web at sites such as the CMS Molecular Biology Resource at sdsc.edu/ResTools/cmshp.html. Any sequence database that contains DNA or protein sequences corresponding to a gene or a segment thereof can be used for sequence analysis. Commonly employed databases include but are not limited to GenBank, EMBL, DDBJ, PDB, SWISS-PROT, EST, STS, GSS, and HTGS.

Parameters for determining the extent of homology set forth by one or more of the aforementioned alignment programs are well established in the art. They include but are not limited top value, percent sequence identity and the percent sequence similarity. P value is the probability that the alignment is produced by chance. For a single alignment, the p value can be calculated according to Karlin et al. (1990) Proc. Natl. Acad. Sci. (USA) 87: 2246. For multiple alignments, the p value can be calculated using a heuristic approach such as the one programmed in BLAST. Percent sequence identify is defined by the ratio of the number of nucleotide or amino acid matches between the query sequence and the known sequence when the two are optimally aligned. The percent sequence similarity is calculated in the same way as percent identity except one scores amino acids that are different but similar as positive when calculating the percent similarity. Thus, conservative changes that occur frequently without altering function, such as a change from one basic amino acid to another or a change from one hydrophobic amino acid to another are scored as if they were identical.

Polypeptides

Another aspect of this invention is directed to soluble G glycoprotein polypeptides of HeV or NiV. The term polypeptide is used broadly herein to include peptide or protein or fragments thereof. By way of example, and not limitation, a soluble HeV G glycoprotein may comprise amino acids 71-604 of the amino acid sequence for a HeV G glycoprotein in Wang, L. F. et al., J. Virol. 74 (21), 9972-9979 (2000) (see also, e.g., Yu, M. et al., Virology 251 (2), 227-233 (1998)). Also by way of example and not limitation, a soluble NiV G glycoprotein may comprise amino acids 71-602 of the amino acid sequence for a NiV G glycoprotein in Harcourt, B H et al., Virology 271: 334-349, 2000 (see also Chua, K. B. et al., Science 288 (5470), 1432-1).

Functional equivalents of these polypeptides are also intended to be encompassed by this invention. By way of example and not limitation functionally equivalent polypeptides possess one or more of the following characteristics: ability to interact or bind the viral host cell receptor, can be produced in oligomeric form or forms, the ability to elicit antibodies (including, but not limited to, viral neutralizing antibodies) capable of recognizing native G Glycoprotein and/or the ability to block or prevent infection of a host cell.

Also intended to be encompassed are peptidomimetics, which include chemically modified peptides, peptide-like molecules containing non-naturally occurring amino acids, peptides and the like, and retain the characteristics of the soluble G glycoprotein polypeptides provided herein. ("Burger's Medicinal Chemistry and Drug Discovery" 5th ed., vols. 1 to 3 (ed. M. E. Wolff; Wiley Interscience 1995).

This invention further includes polypeptides or analogs thereof having substantially the same function as the polypeptides of this invention. Such polypeptides include, but are not limited to, a substitution, addition or deletion mutant of the polypeptide. This invention also encompasses proteins or peptides that are substantially homologous to the polypeptides. A variety of sequence alignment software programs described herein above are available in the art to facilitate determination of homology or equivalence of any protein to a protein of the invention.

The term "analog" includes any polypeptide having an amino acid residue sequence substantially identical to a polypeptide of the invention in which one or more residues have been conservatively substituted with a functionally similar residue and which displays the functional aspects of the polypeptides as described herein. Examples of conservative substitutions include the substitution of one non-polar (hydrophobic) residue such as isoleucine, valine, leucine or methionine for another, the substitution of one polar (hydrophilic) residue for another such as between arginine and lysine, between glutamine and asparagine, between glycine and serine, the substitution of one basic residue such as lysine, arginine or histidine for another, or the substitution of one acidic residue, such as aspartic acid or glutamic acid or another.

The phrase "conservative substitution" also includes the use of a chemically derivatized residue in place of a non-derivatized residue. "Chemical derivative" refers to a subject polypeptide having one or more residues chemically derivatized by reaction of a functional side group. Examples of such derivatized molecules include for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-im-benzylhistidine. Also included as chemical derivatives are those proteins or peptides which contain one or more naturally-occurring amino acid derivatives of the twenty standard amino acids. For examples: 4-hydroxyproline may be substituted for proline; 5-hydroxylysine may be substituted for lysine; 3-methylhistidine may be substituted for histidine; homoserine may be substituted for serine; and ornithine may be substituted for lysine. Polypeptides of the present invention also include any polypeptide having one or more additions and/or deletions or residues relative to the sequence of a any one of the polypeptides whose sequences is described herein.

Two polynucleotide or polypeptide sequences are said to be "identical" if the sequence of nucleotides or amino acids in the two sequences is the same when aligned for maximum correspondence as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O. (1978) A model of evolutionary change in proteins—Matrices for detecting distant relationships. In Dayhoff, M. O. (ed.) Atlas of Protein Sequence and Structure, National Biomedical Research Foundation, Washington D.C. Vol. 5, Suppl. 3, pp. 345-358; Hein J., 1990, Unified Approach to Alignment and Phylogenes pp. 626-645 Methods in Enzymology vol. 183, Academic Press, Inc., San Diego, Calif.; Higgins, D. G. and Sharp, P. M., 1989, CABIOS 5:151-153; Myers, E. W. and Muller W., 1988, CABIOS 4:11-17; Robinson, E. D., 1971, Comb. Theor. 11:105; Santou, N., Nes, M., 1987, Mol. Biol. Evol. 4:406-425; Sneath, P. H. A. and Sokal, R. R., 1973, Numerical Taxonomy the Principles and Practice of Numerical Taxonomy, Freeman Press, San Francisco, Calif.; Wilbur, W. J. and Lipman, D. J., 1983, Proc. Natl. Acad. Sci. USA 80:726-730.

Preferably, the "percentage of sequence identity" is determined by comparing two optimally aligned sequences over a window of comparison of at least 20 positions, wherein the portion of the polypeptide sequence in the comparison window may comprise additions or deletions (i.e. gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical r amino acid residue occurs in both sequences to yield the number of matched positions, dividing the number of matched positions by the total number of positions in the reference sequence (i.e. the window size) and multiplying the results by 100 to yield the percentage of sequence identity.

Expression Vectors

This invention also relates to expression vectors comprising at least one polynucleotide encoding a soluble G glycoprotein protein of the invention. Expression vectors are well known in the art and include, but are not limited to viral vectors or plasmids. Viral-based vectors for delivery of a desired polynucleotide and expression in a desired cell are well known in the art. Exemplary viral-based vehicles include, but are not limited to, recombinant retroviruses (see, e.g., PCT Publication Nos. WO 90/07936; WO 94/03622; WO 93/25698; WO 93/25234; WO 93/11230; WO 93/10218; WO 91/02805; U.S. Pat. Nos. 5,219,740 and 4,777,127), alphavirus-based vectors (e.g., Sindbis virus vectors, Semliki forest virus), Ross River virus, adeno-associated virus (AAV) vectors (see, e.g., PCT Publication Nos. WO 94/12649, WO 93/03769; WO 93/19191; WO 94/28938; WO 95/11984 and WO 95/00655), vaccinia virus (e.g., Modified Vaccinia virus Ankara (MVA) or fowlpox), Baculovirus recombinant system and herpes virus.

Nonviral vectors, such as plasmids, are also well known in the art and include, but are not limited to, yeast and bacterial based plasmids.

Methods of introducing the vectors into a host cell and isolating and purifying the expressed protein are also well known in the art (e.g., *Molecular Cloning: A Laboratory Manual*, second edition (Sambrook, et al., 1989) Cold Spring Harbor Press). Examples of host cells include, but are not limited to, mammalian cells, such as HeLa and CHO cells.

By way of example the vector comprising the polynucleotide encoding the soluble G protein may further comprise a tag polynucleotide sequence to facilitate isolation and/or purification. Examples of tags include but are not limited to, myc-eptiope, S-tag, his-tag, HSV-epitope, V5-epitope, FLAG and CBP. Such tags are commercially available or readily made by methods known to the art.

The vector may further comprise a polynucleotide sequence encoding a linker sequence. Generally the linking sequence is positioned in the vector between the soluble G protein polynucleotide sequence and the polynucleotide tag sequence. Linking sequences can encode random amino acids or can contain functional sites. Examples of linking sequences containing functional sites include but are not limited to, sequences containing the thrombin cleavage site or the enterokinase cleavage site.

By way of example, and not limitation, a soluble G glycoprotein may be generated as described herein using vaccinia virus recombinants in a mammalian cell culture system. Examples of primers that may be used to amplify the desired ectodomain sequence from a Hendra virus or Nipah virus cDNA template, include, but are not limited to, the primers in the Examples.

Antibodies

Examples of antibodies encompassed by the present invention, include, but are not limited to, antibodies specific for HeV G glycoprotein, antibodies specific for NiV G glycoprotein, antibodies that cross react with HeV G glycoprotein and NiV G Glycoprotein and neutralizing antibodies. By way of example a characteristic of a neutralizing antibody includes, but is not limited to, the ability to block or prevent infection of a host cell. The antibodies of the invention may be characterized using methods well known in the art.

The antibodies useful in the present invention can encompass monoclonal antibodies, polyclonal antibodies, antibody fragments (e.g., Fab, Fab', F(ab')2, Fv, Fc, etc.), chimeric antibodies, bispecific antibodies, heteroconjugate antibodies, single chain (ScFv), mutants thereof, fusion proteins comprising an antibody portion, humanized antibodies, and any other modified configuration of the immunoglobulin molecule that comprises an antigen recognition site of the required specificity, including glycosylation variants of antibodies, amino acid sequence variants of antibodies, and covalently modified antibodies. Preferred antibodies are derived from murine, rat, human, primate, or any other origin (including chimeric or humanized antibodies).

Methods of preparing monoclonal and polyclonal antibodies are well know in the art. Polyclonal antibodies can be raised in a mammal, for example, by one or more injections of an immunizing agent and, if desired an adjuvant. Examples of adjuvants include, but are not limited to, keyhole limpet, hemocyanin, serum albumin, bovine thryoglobulin, soybean trypsin inhibitor, Freund complete adjuvant and MPL-TDM adjuvant. The immunization protocol can be determined by one of skill in the art.

The antibodies may alternatively be monoclonal antibodies. Monoclonal antibodies may be produced using hybridoma methods (see, e.g., Kohler, B. and Milstein, C. (1975) *Nature* 256:495-497 or as modified by Buck, D. W., et al., *In Vitro,* 18:377-381 (1982).

If desired, the antibody of interest may be sequenced and the polynucleotide sequence may then be cloned into a vector for expression or propagation. The sequence encoding the antibody of interest may be maintained in vector in a host cell and the host cell can then be expanded and frozen for future use. In an alternative, the polynucleotide sequence may be used for genetic manipulation to "humanize" the antibody or to improve the affinity, or other characteristics of the antibody (e.g., genetically manipulate the antibody sequence to obtain greater affinity to the G glycoprotein and/or greater efficacy in inhibiting the fusion of the Hendra or Nipah virus to the host cell receptor.).

The antibodies may also be humanized by methods known in the art. (See, for example, U.S. Pat. Nos. 4,816,567; 5,807,715; 5,866,692; 6,331,415; 5,530,101; 5,693,761; 5,693,762; 5,585,089; and 6,180,370). In yet another alternative, fully human antibodies may be obtained by using commercially available mice that have been engineered to express specific human immunoglobulin proteins.

In another alternative, antibodies may be made recombinantly and expressed using any method known in the art. By way of example, antibodies may be made recombinantly by phage display technology. See, for example, U.S. Pat. Nos. 5,565,332; 5,580,717; 5,733,743; and 6,265,150; and Winter et al., *Annu. Rev. Immunol.* 12:433-455 (1994). Alternatively, the phage display technology (McCafferty et al., *Nature* 348:552-553 (1990)) can be used to produce human antibodies and antibody fragments in vitro. Phage display can be performed in a variety of formats; for review see, e.g., Johnson, Kevin S. and Chiswell, David J., *Current Opinion in Structural Biology* 3:564-571 (1993). By way of example, a soluble G glycoprotein as described herein may be used as an antigen for the purposes of isolating recombinant antibodies by these techniques.

Antibodies may be made recombinantly by first isolating the antibodies and antibody producing cells from host animals, obtaining the gene sequence, and using the gene sequence to express the antibody recombinantly in host cells (e.g., CHO cells). Another method which may be employed is to express the antibody sequence in plants (e.g., tobacco) or transgenic milk. Methods for expressing antibodies recombinantly in plants or milk have been disclosed. See, for example, Peeters, et al. *Vaccine* 19:2756 (2001); Lonberg, N. and D. Huszar *Int. Rev. Immunol* 13:65 (1995); and Pollock, et al., *J Immunol Methods* 231:147 (1999). Methods for making derivatives of antibodies, e.g., humanized, single chain, etc. are known in the art.

The antibodies of the invention can be bound to a carrier by conventional methods, for use in, for example, isolating or purifying Hendra or Nipah G glycoproteins or detecting Hendra or Nipah G glycoproteins in a biological sample or specimen. Alternatively, by way of example, the neutralizing antibodies of the invention may be administered as passive immunotherapy to a subject infected with or suspected of being infected with Hendra or Nipah virus. A "subject," includes but is not limited to humans, simians, farm animals, sport animals and pets. Veterinary uses are also encompassed by the invention.

Diagnostics

The soluble G glycoproteins and/or antibodies of the invention may be used in a variety of immunoassays for Hendra and Nipah virus. The recombinant expressed soluble G glycoproteins of the invention can be produced with high quality control and are suitable as a antigen for the purposes of detecting antibody in biological samples. By way of example, and not limitation, a soluble HEV or NiV G glycoprotein or combinations thereof could be used as antigens in an ELISA assay to detect antibody in a biological sample from a subject.

Vaccines

This invention also relates to vaccines for Hendra and Nipah virus. In one aspect the vaccines are DNA based vaccines. One skilled in the art is familiar with administration of expression vectors to obtain expression of an exogenous protein in vivo. See, e.g., U.S. Pat. Nos. 6,436,908; 6,413,942; and 6,376,471. Viral-based vectors for delivery of a desired polynucleotide and expression in a desired cell are well known in the art and non-limiting examples are described herein. In another aspect, the vaccines are protein-based and comprises one or more fragments of the G protein of Hendra or Nipah virus. Preferred fragments are the ectodomain, and functional portions thereof, and also, portions that are specifically reactive to neutralizing antibodies. Portions that are so reactive are depicted in FIG. 14. Vaccines may also be antibody-based vaccines for more immediate treatment as well as prophylaxis against infection.

Administration of expression vectors includes local or systemic administration, including injection, oral administration, particle gun or catheterized administration, and topical administration. Targeted delivery of therapeutic compositions containing an expression vector, or subgenomic polynucleotides can also be used. Receptor-mediated DNA delivery techniques are described in, for example, Findeis et al., *Trends Biotechnol*. (1993) 11:202; Chiou et al., *Gene Therapeutics: Methods And Applications Of Direct Gene Transfer* (J. A. Wolff, ed.) (1994); Wu et al., *J. Biol. Chem.* (1988) 263:621; Wu et al., *J. Biol. Chem.* (1994) 269:542; Zenke et al., *Proc. Natl. Acad. Sci. USA* (1990) 87:3655; Wu et al., *J. Biol. Chem.* (1991) 266:338.

Non-viral delivery vehicles and methods can also be employed, including, but not limited to, polycationic condensed DNA linked or unlinked to killed adenovirus alone (see, e.g., Curiel, *Hum. Gene Ther.* (1992) 3:147); ligand-linked DNA (see, e.g., Wu, *J. Biol. Chem*. (1989) 264:16985); eukaryotic cell delivery vehicles cells (see, e.g., U.S. Pat. No. 5,814,482; PCT Publication Nos. WO 95/07994; WO 96/17072; WO 95/30763; and WO 97/42338) and nucleic charge neutralization or fusion with cell membranes. Naked DNA can also be employed. Exemplary naked DNA introduction methods are described in PCT Publication No. WO 90/11092 and U.S. Pat. No. 5,580,859. Liposomes that can act as gene delivery vehicles are described in U.S. Pat. No. 5,422,120; PCT Publication Nos. WO 95/13796; WO 94/23697; WO 91/14445; and EP 0524968. Additional approaches are described in Philip, *Mol. Cell Biol.* (1994) 14:2411, and in Woffendin, *Proc. Natl. Acad. Sci.* (1994) 91:1581.

For human administration, the codons comprising the polynucleotide encoding a soluble G glycoprotein may be optimized for human use.

In another aspect of the invention, a soluble HeV or NiV G glycoprotein or combinations thereof are used as a subunit vaccine. The soluble HeV or NiV G glycoprotein or combination thereof may be administered by itself or in combination with an adjuvant. Examples of adjuvants include, but are not limited, aluminum salts, water-in-soil emulsions, oil-in-water emulsions, saponin, QuilA and derivatives, iscoms, liposomes, cytokines including gamma interferon or interleukin 12, DNA, microencapsulation in a solid or semi-solid particle, Freunds complete and incomplete adjuvant or active ingredients thereof including muramyl dipeptide and analogues, DEAE dextran/mineral oil, Alhydrogel, Auspharm adjuvant, and Algammulin.

The subunit vaccine comprising soluble HeV or NiV G glycoprotein or combinations thereof can be administered orally, intravenously, subcutaneously, intraarterially, intramuscularly, intracardially, intraspinally, intrathoracically, intraperitoneally, intraventricularly, sublingually, and/or transdermally.

Dosage and schedule of administration can be determined by methods known in the art. Efficacy of the soluble HeV or NiV G glycoprotein or combinations thereof as a vaccine for Hendra, Nipah or related *Henipavirus* viruses may also be evaluated by methods known in the art.

Pharmaceutical Compositions

The polynucleotides, polypetides and antibodies of the invention can further comprise pharmaceutically acceptable carriers, excipients, or stabilizers known in the art (*Remington: The Science and practice of Pharmacy* 20th Ed. (2000) Lippincott Williams and Wilkins, Ed. K. E. Hoover.), in the form of lyophilized formulations or aqueous solutions. Acceptable carriers, excipients, or stabilizers are nontoxic to recipients at the dosages and concentrations, and may comprise buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrans; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG). Pharmaceutically acceptable excipients are further described herein.

The compositions used in the methods of the invention generally comprise, by way of example and not limitation, and effective amount of a polynucleotide or polypeptide (e.g., an amount sufficient to induce an immune response) of the invention or antibody of the invention (e.g., an amount of a neutralizing antibody sufficient to mitigate infection, alleviate a symptom of infection and/or prevent infection).

The pharmaceutical composition of the present invention can further comprise additional agents that serve to enhance and/or complement the desired effect. By way of example, to enhance the immunogenicity of a soluble G polypeptide of the invention being administered as a subunit vaccine, the pharmaceutical composition may further comprise an adjuvant. Examples of adjuvants are provided herein.

Also by way of example, an not limitation, if a soluble G protein polypeptide of the invention is being administered to augment the immune response in a subject infected with or suspected of being infected with Hendra or Nipah and/or if antibodies of the present invention are being administered as a form of passive immunotherapy the composition can further comprise, for example, other therapeutic agents (e.g., antiviral agents)

Diagnostic Kits

The invention also provides diagnostic kits for use in the instant methods. Kits of the invention include one or more containers comprising by way of example, and not limitation, polynucleotides encoding a soluble G HeV or NiV G glycoprotein or combinations thereof, a soluble G HeV or NiV G glycoprotein or combinations thereof and/or antibodies of the invention and instructions for use in accordance with any of the methods of the invention described herein.

Generally, these instructions comprise a description of administration or instructions for performance of an assay. The containers may be unit doses, bulk packages (e.g., multi-dose packages) or sub-unit doses. Instructions supplied in the kits of the invention are typically written instructions on a label or package insert (e.g., a paper sheet included in the kit), but machine-readable instructions (e.g., instructions carried on a magnetic or optical storage disk) are also acceptable.

The kits of this invention are in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump. A kit may have a sterile access port (for example the container may be an intravenous solution bag or a vial having a stopper pierceable by a hypodermic injection needle). The container may also have a sterile access port (for example the container may be an intravenous solution bag or a vial having a stopper pierceable by a hypodermic injection needle). Kits may optionally provide additional components such as buffers and interpretive information. Normally, the kit comprises a container and a label or package insert(s) on or associated with the container.

The following examples illustrate only certain and not all embodiments of the invention, and thus, should not be viewed as limiting the scope of the invention.

EXAMPLES

Example 1

Vector Constructs

Vectors were constructed to express transmembrane/cytoplasmic tail-deleted HeV G or NiV G. The cloned cDNAs of full-length HeV or NiV G protein were amplified by PCR to generate fragments about 2600 bp encoding the transmembrane domain/cytoplasmic tail-deleted HeVG or NiV G protein.

The following oligonucleotide primers were synthesized for amplification of HeV G. sHGS: 5'-GTCGACCACCATGCAAAATTACACCAGAACGACTGATAAT-3' (SEQ ID NO 1). sHGAS: 5'-GTTTAAACGTCGACCAATCAACTCTCTGAACATTG GGCAGGTATC-3'. (SEQ ID NO 2).

The following oligonucleotide primers were synthesized for amplification of NiV G. sNGS: 5'-CTCGAGCACCATGCAAAATTACACAAGATCAACAGACAA-3' (SEQ ID NO 3). sNGAS: 5'-CTCGAGTAGCAGCCGGATCAAGCTTATGTACATT GCTCTGGTATC-3'. (SEQ ID NO 4).

All PCR reactions were done using Accupol DNA polymerase (PGS Scientifics Corp., Gaithersburg, Md.) with the following settings: 94° C. for 5 min initially and then 94° C. for 1 minute, 56° C. for 2 minutes, 72° C. for 4 minutes; 25 cycles. These primers generated a PCR product for the sHeV G ORF flanked by Sal 1 sites and the sNiV G ORF flanked by Xho 1 sites. PCR products were gel purified (Qiagen, Valencia, Calif.). After gel purification, sHeV G and sNiV G were subcloned into a TOPO vector (Invitrogen Corp., Carlsbad, Calif.).

PSectag2B (Invitrogen Corp.) was purchased and modified to contain a S-peptide tag or a myc-epitope tag. Overlapping oligonucleotides were synthesized that encoded the sequence for the S-peptide and digested Kpn 1 and EcoR1 overhangs.

```
SPEPS:
                                          (SEQ ID NO 5)
5'-CAAGGAGACCGCTGCTGCTAAGTTCGAACGCCAGCACATGGATT
CT-3'.

SPEPAS:
                                          (SEQ ID NO 6)
5'AATTAGAATCCATGTGCTGGCGTTCGAACTTAGCAGCAGCGGTCT
CCTTGGTAC-3'..
```

Overlapping oligonucleotides were synthesized that encoded the sequence for the myc-epitope tag and digested Kpn 1 and EcoR1 overhangs.

```
MTS:
                                          (SEQ ID NO 7)
5'-CGAACAAAAGCTCATCTCAGAAGAGGATCTG-3'.

MTAS
                                          (SEQ ID NO 8)
5'-AATTCAGATCCTCTTCTGAGATGAGCTTTTGTTCGGTAC-3'..
```

64 ρmol SPEPS and 64 ρmol SPEPAS were mixed and heated to 65° C. for 5 minutes and cooled slowly to 50° C. 64 ρmol MTS and 64 ρmol MTAS were mixed and heated to 65° C. for 5 minutes and cooled slowly to 50° C. The two mixtures were diluted and cloned into Kpn1-EcoR1 digested pSecTag2B to generate S-peptide modified pSecTag2B or myc-epitope modified pSecTag2B. All constructs were initially screened by restriction digest and further verified by sequencing.

The TOPO sG construct was digested with Sal 1 gel purified (Qiagen) and subcloned in frame into the Xho 1 site of the S-peptide modified pSecTag2B or myc-epitope modified pSecTag2B. All constructs were initially screened by restriction digest and further verified by sequencing.

The Igκ leader-5-peptide-s HeVG ($sG_{S-tag}$) and the Igκ leader-myc tag-sHeVG ($sG_{myc-tag}$) constructs were then subcloned into the vaccinia shuttle vector pMCO2 [Carroll, 1995]. Oligonucleotide SEQS: 5'-TCGACCCACCATGGAGACAGACACACTCCTGCTA-3' (SEQ ID NO 9) was synthesized and used in combination with oligonucleotide sHGAS to amplify by PCR the $sG_{S-tag}$ and $sG_{myc-tag}$. All PCR reactions were done using Accupol DNA polymerase (PGS Scientifics Corp.) with the following settings: 94° C. for 5 min initially and then 94° C. for 1 minute, 56° C. for 2 minutes, 72° C. for 4 minutes; 25 cycles. These primers generated PCR products flanked by Sal 1 sites. PCR products were gel purified (Qiagen). After gel purification, $sG_{S-tag}$ and $sG_{myc-tag}$ were subcloned into a TOPO vector (Invitrogen Corp.). sG S-tag and sG myc-tag were digested with Sal 1 and subcloned into the Sal 1 site of pMCO2. All constructs were initially screened by restriction digest and further verified by sequencing. The polypeptide structures of HeV sG S-tag and HeV sG myc-tag are depicted in a representative drawing in FIG. 6.

Example 2

Protein Production of Soluble G Protein

For protein production the genetic constructs were used to generate recombinant poxvirus vectors (vaccinia virus, strain WR). Recombinant poxvirus was then obtained using standard techniques employing tk-selection and GUS staining (6). Briefly, CV-1 cells were transfected with either pMCO2 sHeV G fusion or pMCO2 sNiV G fusion using a calcium phosphate transfection kit (Promega, Corp., Madison, Wis.). These monolayers were then infected with Western Reserve (WR) wild-type strain of vaccinia virus at a multiplicity of infection (MOI) of 0.05 PFU/cell. After 2 days the cell pellets were collected as crude recombinant virus stocks. $TK^-$ cells were infected with the recombinant crude stocks in the presence of 25 μg/ml 5-Bromo-2'-deoxyuridine (BrdU) (Calbiochem, La Jolla, Calif.). After 2 hours the virus was replaced with an EMEM-10 overlay containing 1% low melting point (LMP) agarose (Life Technologies, Gaithersburg, Md.) and 25 μg/ml BrdU. After 2 days of incubation an additional EMEM-10 overlay containing 1% LMP agarose, 25 μg/ml BrdU, and 0.2 mg/ml 5-Bromo-4-chloro-3-indolyl-β-D-glucuronic acid (X-GLUC) (Clontech, Palo Alto, Calif.) was added. Within 24-48 hours blue plaques were evident, picked and subject to two more rounds of double selection plaque purification. The recombinant vaccinia viruses vKB16 (sHeV G fusion) and vKB22 (sNiV G fusion) were then amplified and purified by standard methods. Briefly, recombinant vaccinia viruses are purified by plaque purification, cell-culture amplification, sucrose cushion pelleting in an ultracentrifuge and titration by plaque assay. Expression of sHeV G was verified in cell lysates and culture supernatants (FIG. 1).

As shown in FIG. 1, vaccinia virus encoding either a myc-tag or S-tag soluble HeV G was produced by metabolic labeling in HeLa cells. Control is wild-type HeV G. Specific precipitation of each sG construct is shown by precipitation from either lysates or supernatants using myc MAb or S-beads.

Example 3

Properties of Soluble G Protein

To demonstrate that the recombinant expressed, soluble, purified G (sHeV G) retained desirable properties (e.g. native structural features such as receptor binding competence), it has been demonstrated that pre-incubation of target cells with affinity-purified sHeV G results in a dose-dependent inhibition of virus-mediated fusion in several different cell lines that are susceptible to virus-mediated fusion and infection (FIG. 2).

For purification of soluble G glycoproteins, HeLa cells were infected with vKB15 or vKB16 (moi=3) for 2 hours. After infection the virus was removed and serum-free Opti- Mem medium (Invitrogen, Corp.) was added. After 36 hours, the supernatants were removed and clarified by centrifugation. A S-protein column was poured with 15 ml of S-protein agarose (Novagen) in a XK26 column (Amersham Pharmacia Biotech, Piscataway, N.J.). The S-protein column was washed with 10 bed volumes of PBS. The supernatant from vKB16-infected cells was passed over S-protein agarose column, the column was washed with 10 bed volumes of PBS, and the $sG_{S\text{-}tag}$ was eluted with 1 bed volume of 0.2M citrate pH=2 into 20 ml 1M Tris pH=8. Lentil lectin Sepharose B was purchased (Amersham Pharmacia Biotech) and a 25 ml XK26 column was poured. The supernatants from vKB15-infected cells were passed over the lentil lectin column, the column was washed with 10 bed volumes PBS, and the $sG_{myc\text{-}tag}$ was eluted with 1 bed volume of 0.2M glycine pH=2.5 into 2 ml 1M Tris pH=8. Both eluates were then concentrated using 30 kDA Centricon centrifugal filter units (Millipore, Billerica, Mass.) and filter sterilized. Protein concentrations were calculated using SDS/PAGE, Commassie brilliant blue R-250 staining and densitometry analysis with NIH image 1.62 software.

Figures 2C, 2D:
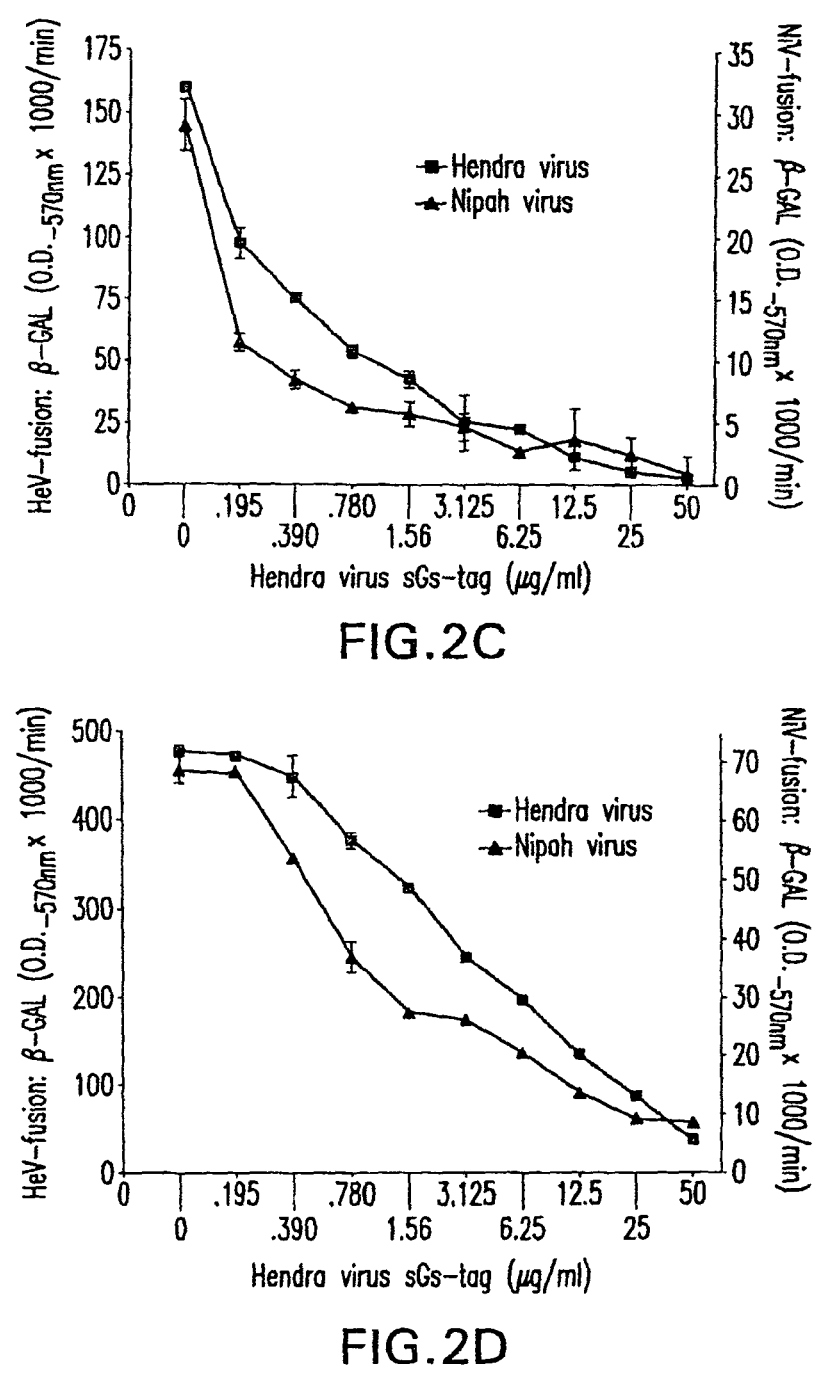
Figures 2E, 2F:
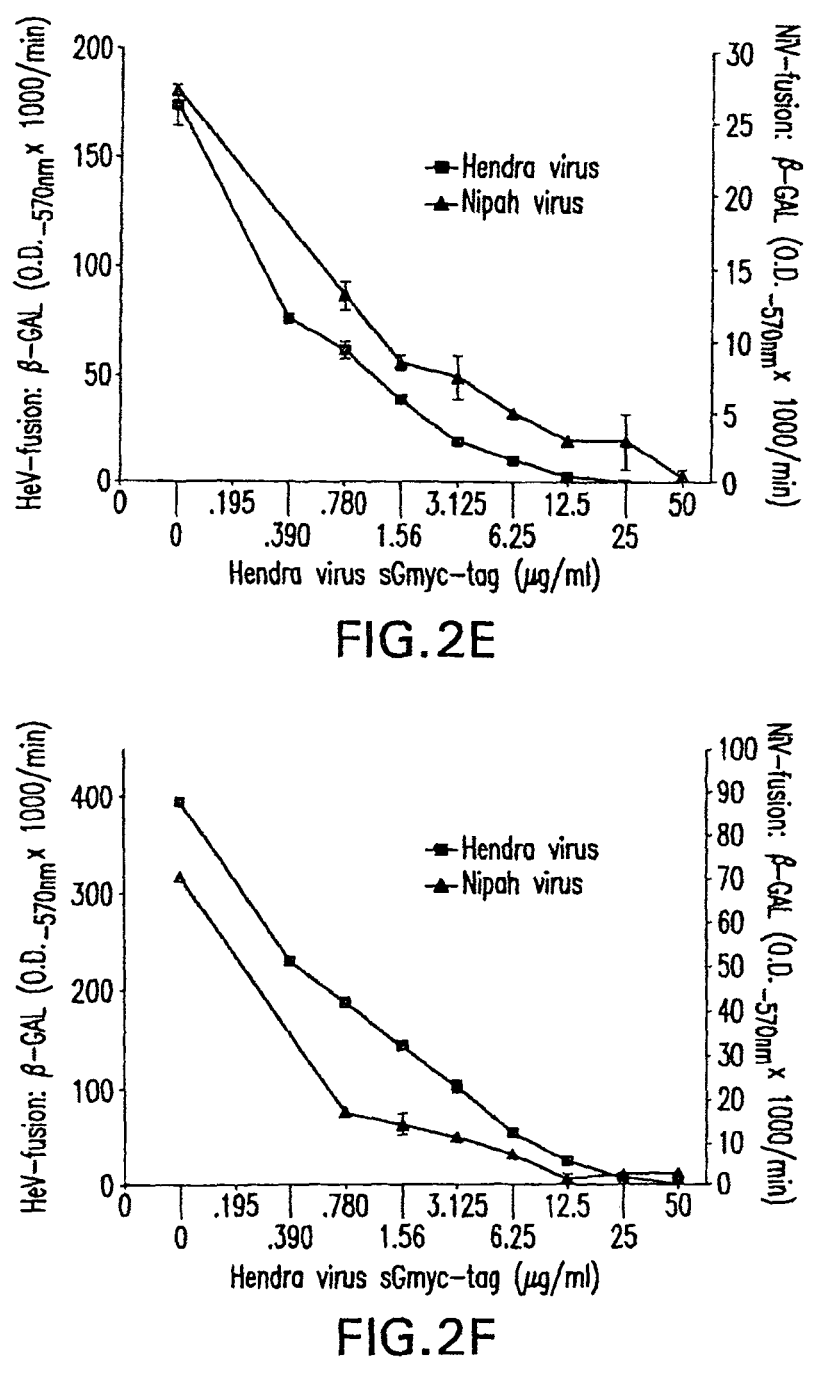

As shown in FIG. 2, soluble HeV G envelope glycoprotein (either the S-tag or myc-tag versions) blocks both HeV and NiV-mediated cell-cell fusion. Dose response inhibition of HeV and NiV cell-cell fusion was conducted by pre-incubating target cells with the indicated amount of purified sG for 30 min at room temperature. Effector cells expressing either HeV or NiV F and G were added and fusion was allowed to proceed for 2.5 h at 37° C. Reaction mixes were processed for β-gal production using the β-gal reporter gene assay. Assays were carried out in duplicate. Panels A and B show that crude sHeV G (S-tag) containing supernatant can potently block HeV-mediated fusion in two alternant cell types, while a control supernatant from WR infected cells (non-recombinant vaccinia virus infected) has no effect. Panels C and D: Inhibition of HeV and NiV-mediated fusion by sG S-tag in U373 cells (Panel C) or PCI 13 cells (Panel D). Panels E and F: Inhibition of HeV- and NiV-mediated fusion by purified sG myc-tag in U373 cells (Panel E) or PCI 31 cells (Panel F).

Figure 3A:
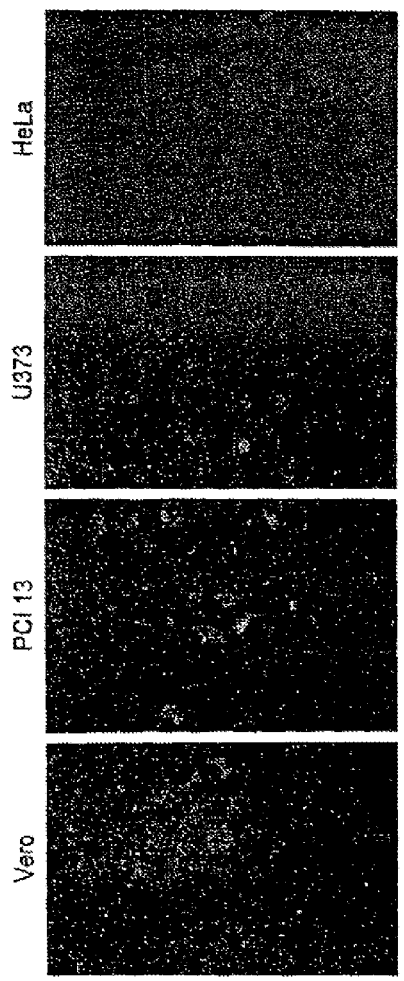
Figure 3B:
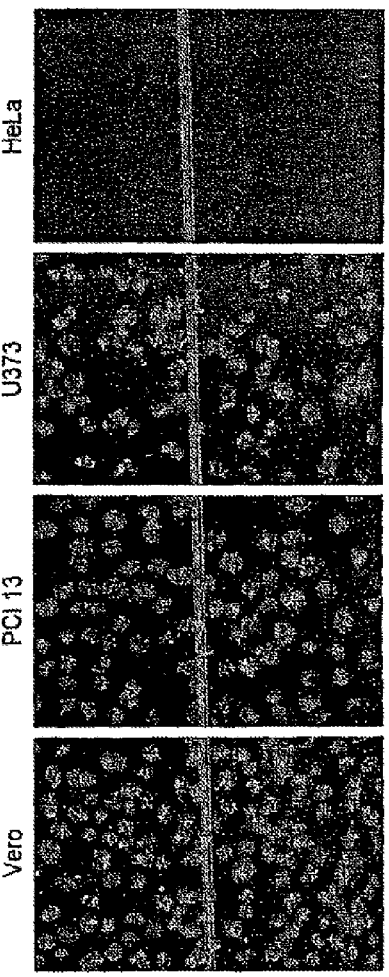
Figure 4:
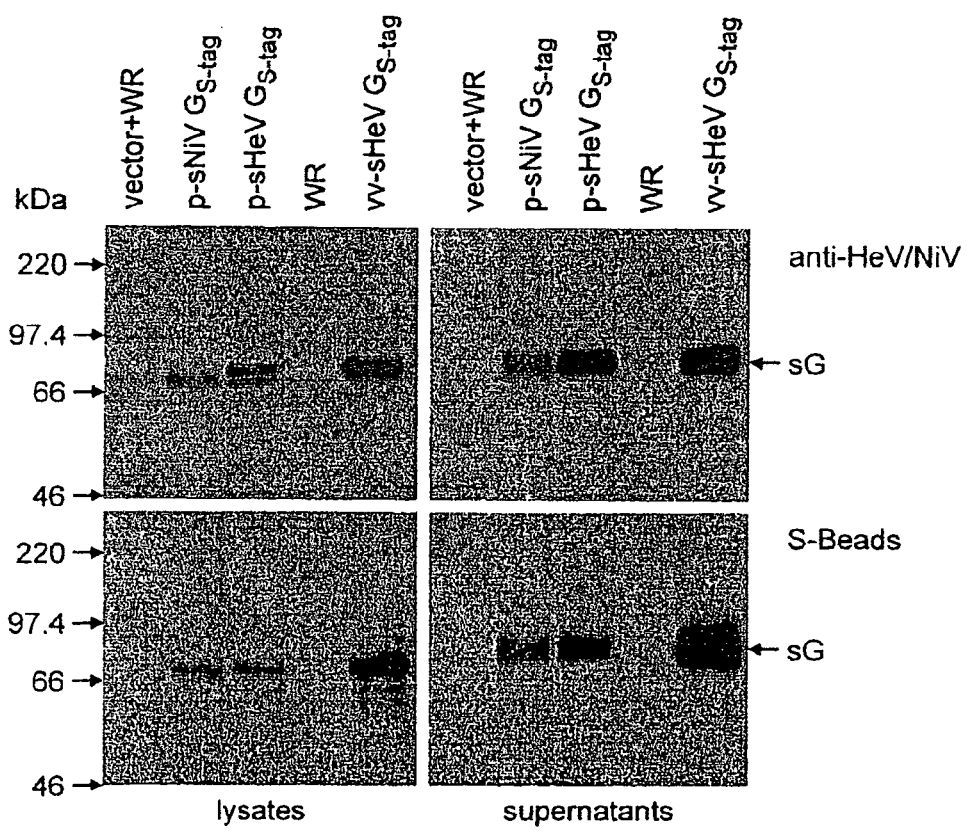
Figure 5A:
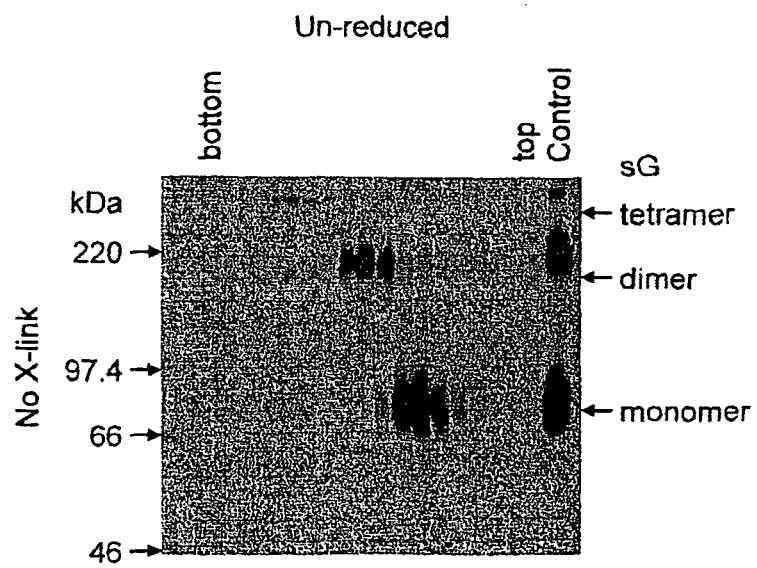
Figure 5B:
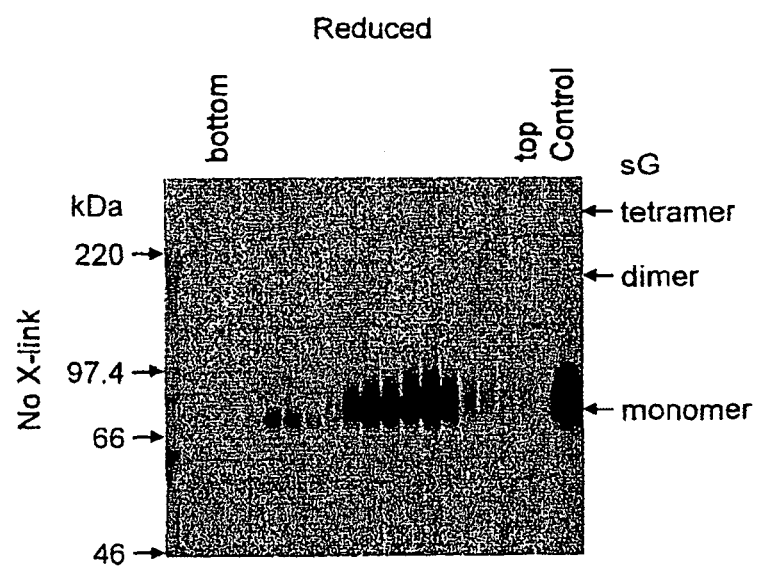
Figure 5C:
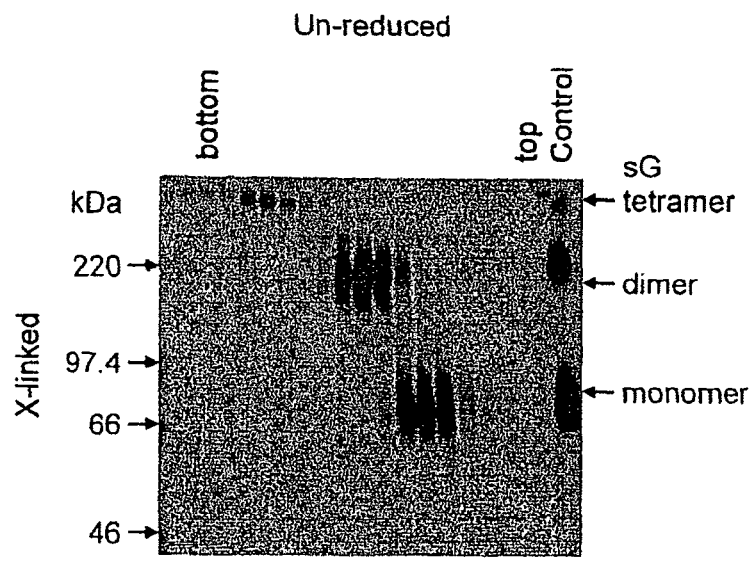
Figure 5D:
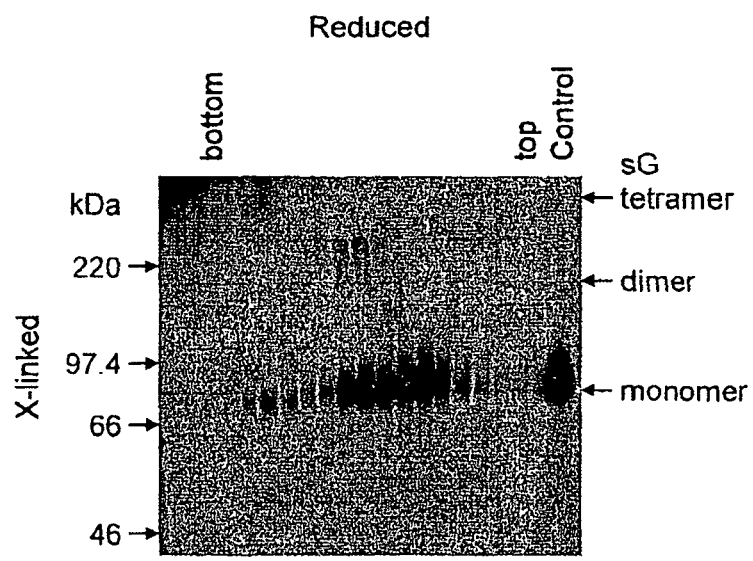

As additional evidence, indirect immunofluorescence was performed that demonstrated sHeV G can specifically bind to cell lines that are susceptible to virus-mediated fusion and infection (FIG. 3). sHeV G is unable to bind to HeLa cells, a non-permissive cell line for HeV and NiV-mediated fusion and virus infection. These data suggest that sHeV G inhibits HeV-mediated fusion by binding to the putative receptor on target cells thus blocking subsequent attachment and fusion of HeV G and F expressing effector cells. The interaction of sHeV G with the putative HeV receptor may be a useful tool for receptor purification and identification. Since the soluble G glycoprotein can be expressed and purified and also exhibits biochemical features similar to that what would be expected from the native G glycoprotein making it an ideal subunit immunogen for the elicitation of virus-neutralizing antibodies. A similar sG construct has been made using the same S-tag approach (see methods above) using the coding sequence of the G envelope glycoprotein of Nipah virus. This sNiV G (S-tag) has been cloned and expressed and is shown in FIG. 4.

A final analysis of the sHeV G (S-tag) envelope glycoprotein was made to evaluate the predicted oligomeric nature of the protein. The retention of some oligomeric properties of a soluble and secreted G glycoprotein may be important in retaining critical immunological or biochemical features as discussed in the introduction above. FIG. 5 shows an analysis of secreted sHeV G (S-tag) glycoprotein by sucrose gradient fractionation which identifies monomeric, dimeric and tetrameric forms of the G glycoprotein. Both cross-linked and non-cross-linked materials were analyzed. The results indicate that monomeric, dimeric, and some tetrameric sG comprises the sG preparation, and this is in agreement with findings on soluble and full-length versions of other paramyxovirus H and HN attachment glycoproteins (discussed above). These three species could be separated by preparative size exclusion chromatography techniques if desired.

Example 4

Characterization of Soluble and Secreted HeV G

Figure 7:
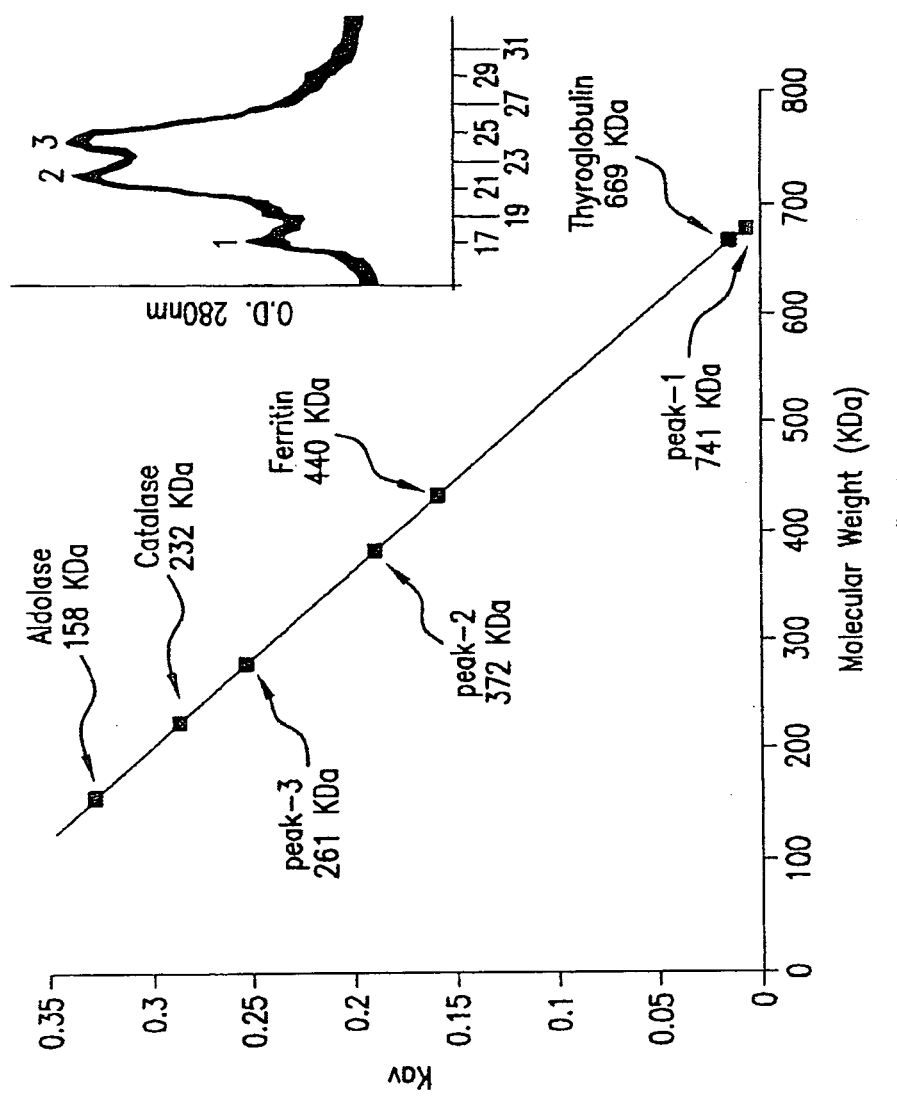

It was next sought to determine if the secreted sG was oligomeric in nature. The apparent molecular weight of purified sG material was first examined using size exclusion chromatography with a calibrated Superdex 200 analytical grade column 10/300. A 500 µg aliquot of either $sG_{S\text{-}tag}$ or $sG_{myc\text{-}tag}$ was passed over the Superdex 200 and fractions were collected using the same methods employed for the high molecular weight standards. Essentially identical results were observed with both the $sG_{S\text{-}tag}$ and $sG_{myc\text{-}tag}$ glycoproteins, and the results shown in FIG. 7 are those for $sG_{S\text{-}tag}$. The locations of the protein standards and the three major species of sG are indicated in the figure. The inset shows the profile of separated sG. The analysis of purified $sG_{S\text{-}tag}$ in seven independent separation experiments indicated two major peaks with apparent molecular weights of ~372 KDa+/−19 KDa (~60% of the material) and ~261 KDa+/−47 KDa (~35% of the material), and one minor peak of ~741 KDa+/−40 KDa (~5% of the material). These results indicated that at least some of the material would be oligomeric in nature, consistent with the glycoprotein's expected structure. However, from prior experience in the preparation and analysis of soluble virus-derived membrane glycoproteins, such as gp120 from HIV-1, such molecular weight calculations derived from size-exclusion chromatography analysis may be over-estimated.

Figure 8A:
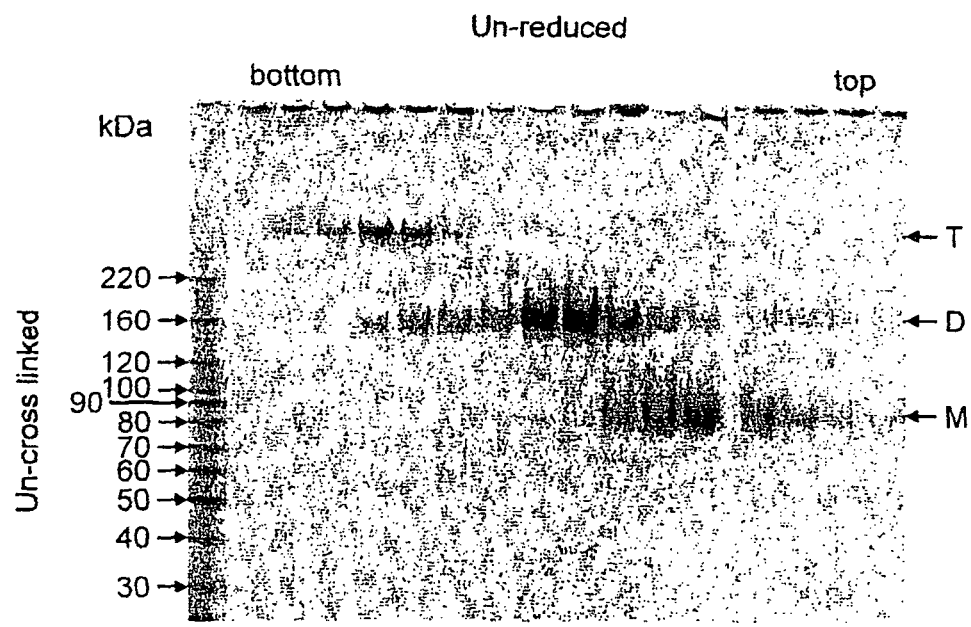
Figure 8B:
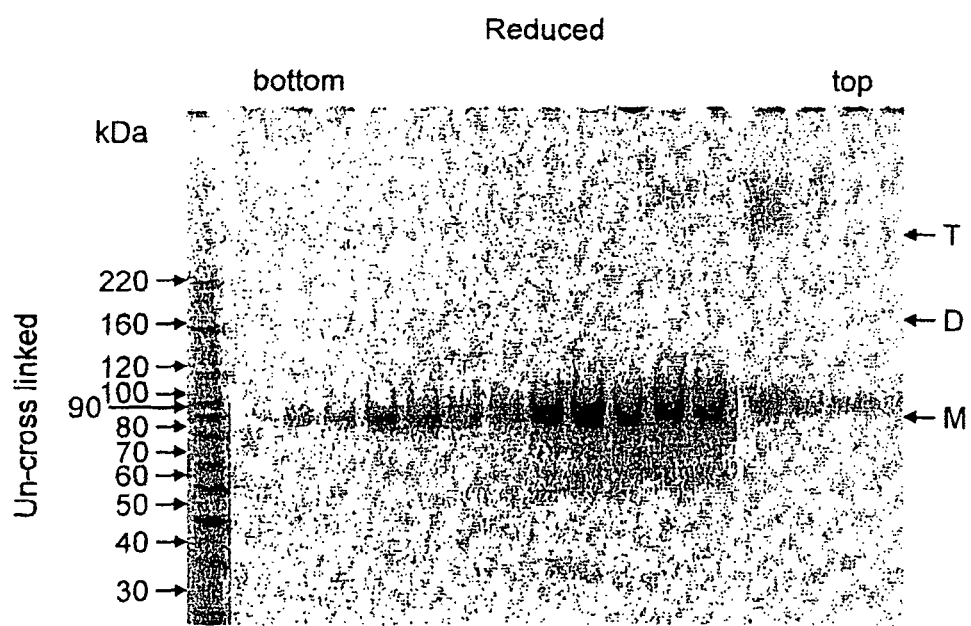
Figure 8C:
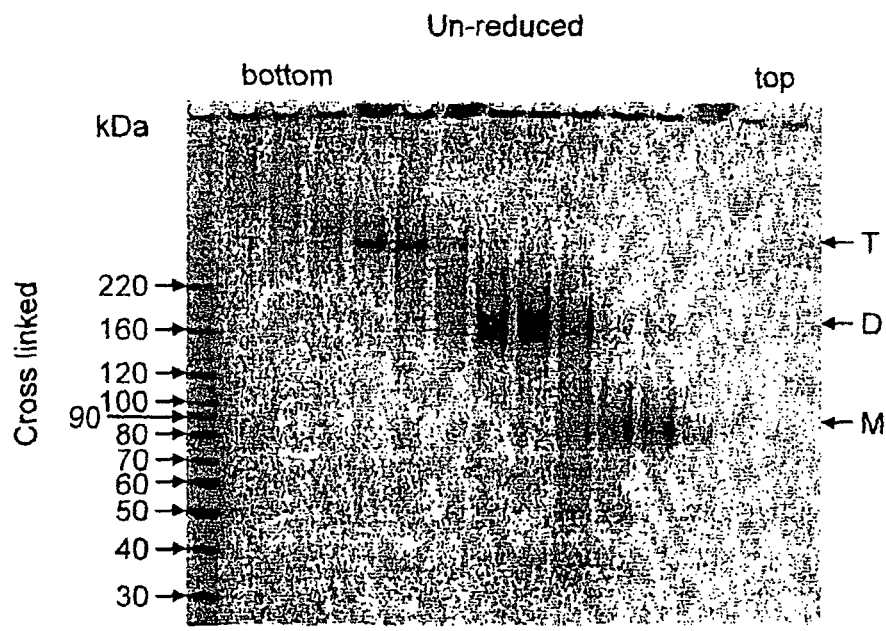
Figure 8D:
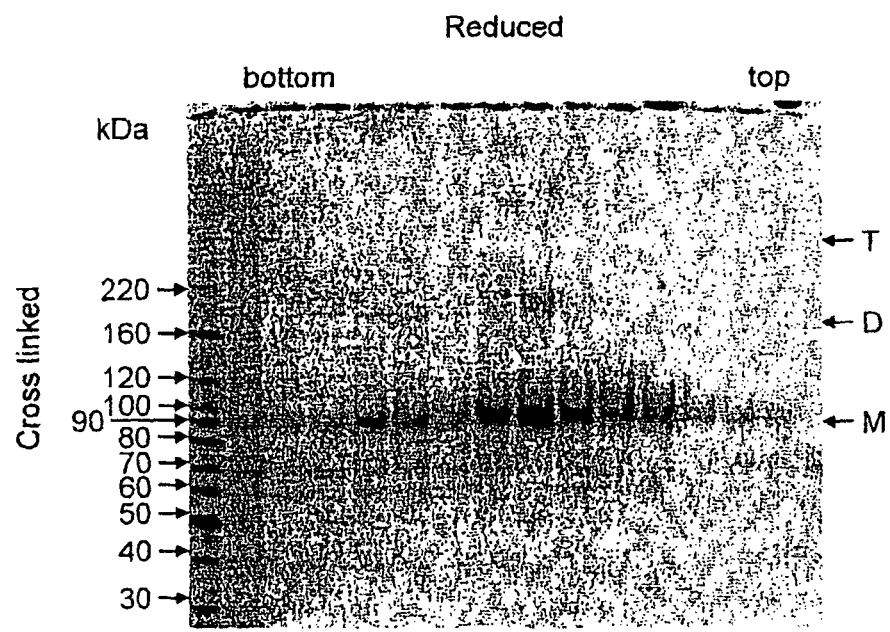
Figure 9A:
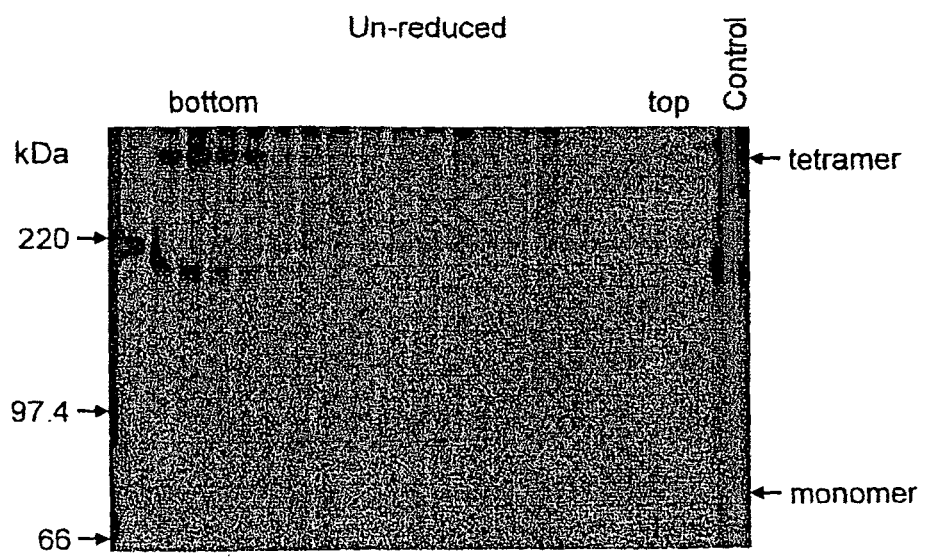
Figure 9B:
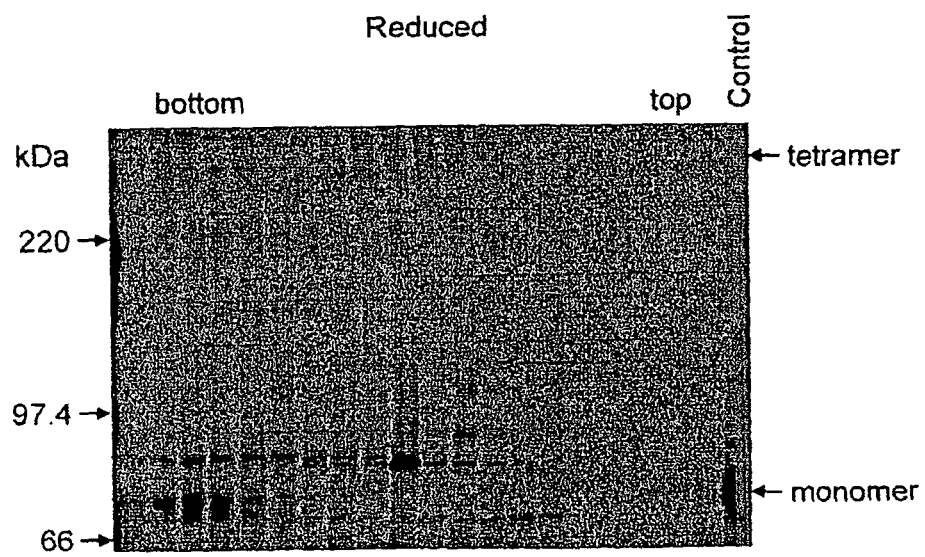
Figure 12:
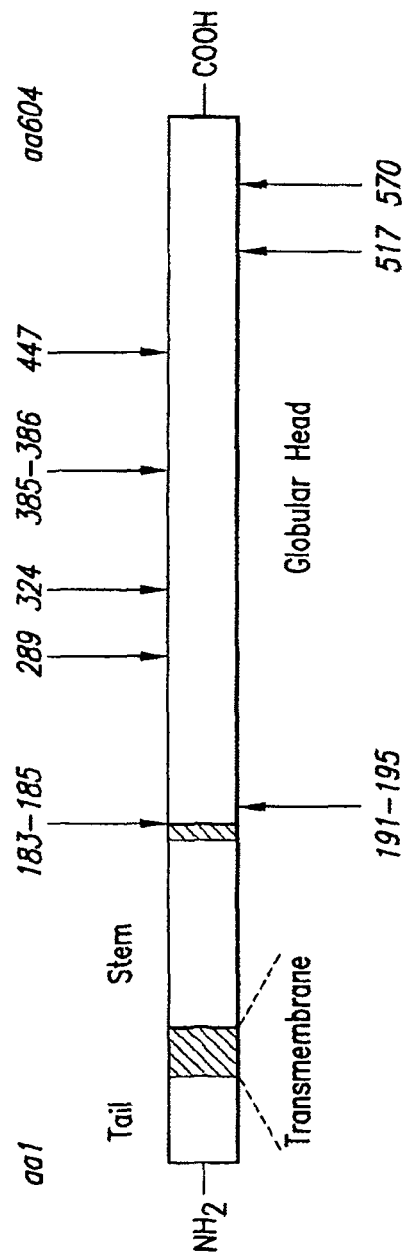
FIG. 12 shows the linear structure of the sG protein.
Figure 13:
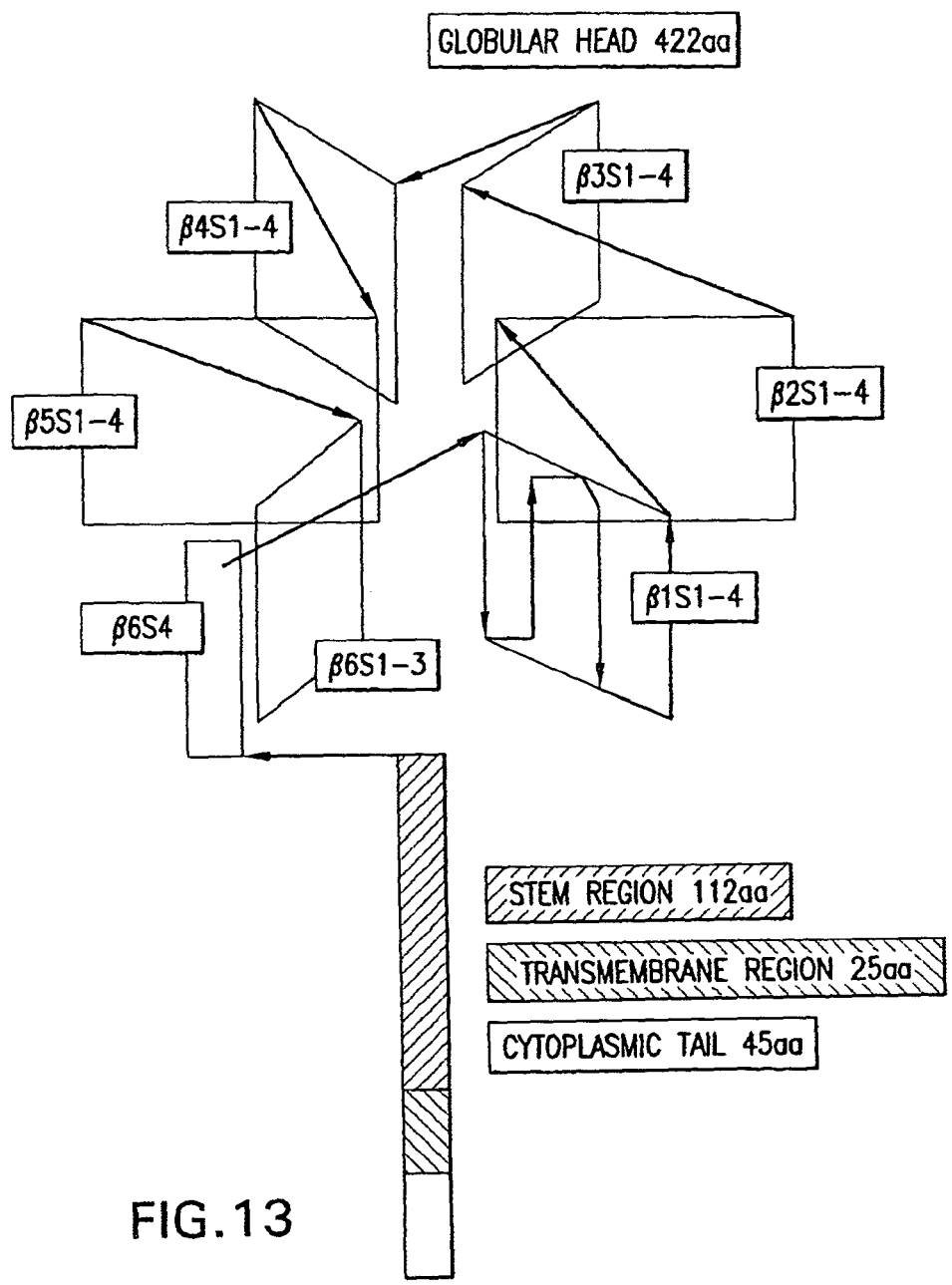
FIG. 13 shows a three dimensional structure of the sG protein.

To further characterize the apparent oligomeric species of sG, $sG_{S\text{-}tag}$ was analyzed using sucrose gradient densitometry. For this analysis, the $sG_{S\text{-}tag}$ glycoprotein was chosen because it can be affinity-precipitated with S-protein agarose circumventing the need for specific MAb. FIG. 8 depicts the oligomeric profiles of metabolically labeled $sG_{S\text{-}tag}$ isolated from the supernatant of expressing cells. Following brief centrifugation to remove any cellular debris the supernatant was concentrated and buffer replaced with PBS as described herein. Prior to separation in the sucrose gradient, half of the supernatant was cross-linked with DTSSP, a reducible cross-linker, and uncross-linked and cross-linked material were loaded onto two separate sucrose gradients. After fractionation of each gradient, the fractions were split into 2 tubes, precipitated with S-protein agarose, washed and resuspended in SDS sample buffer, one set with and one set without β-mercaptoethanol and all four sets of fractions then analyzed by SDS-PAGE. FIGS. 8A and 8B are uncross-linked $sG_{S\text{-}tag}$ separated on the sucrose gradient, fractionated, and immunoprecipitated. In FIG. 8A, the fractions were resolved on SDS-PAGE in the absence of β-mercaptoethanol, whereas in FIG. 8B, the fractions were resolved on SDS-PAGE in the presence of β-mercaptoethanol. FIGS. 8C and 8D are cross-linked $sG_{S\text{-}tag}$ separated on the sucrose gradient, fractionated, and immunoprecipitated. In FIG. 8C, the fractions were resolved on SDS-PAGE in the absence of β-mercaptoethanol whereas in FIG. 8D, the fractions were resolved on SDS-PAGE in the presence of β-mercaptoethanol. The starting material for each gradient was also run on each gel in the presence or absence β-mercaptoethanol and is illustrated as control. From the data shown in FIGS. 8A and 8C, it was determined that for both the uncross-linked and cross-linked $sG_{S\text{-}tag}$, there are three distinct species of sG present. Based on the apparent molecular weights of sG in each of the fractions across each of the gradients, these three species likely represent monomer, dimer and tetramer. In addition, the immediate cross-linking of the sG with DTSSP prior to gradient centrifugation did not significantly increase the amount of either the tetrameric or dimeric species. The analysis of the non-cross-linked, un-reduced and reduced sG clearly indicates that the dimeric oligomer is disulfide linked, which was anticipated based on data derived from other paramyxovirus attachment glycoproteins (36, 44). The dimers of other paramyxovirus attachment glycoproteins have been shown to form a tetramer on the surface of infected cells, and it is generally believed that the native oligomeric structure is a dimer of dimers. To analyze this possibility here, full-length HeV G was expressed and metabolically labeled in HeLa cells (a receptor-negative cell line) and performed a similar experiment and sucrose gradient analysis. Following either a cross-linking procedure, or no treatment, of surface-expressed HeV G on intact cells, the cells were lysed with non-ionic detergent, lysates clarified by centrifugation, and the surface-expressed HeV G preparations analyzed by sucrose gradient centrifugation. Fractions were analyzed by immunoprecipitation with polyclonal anti-HeV rabbit sera followed by Protein G-Sepharose and resolved on SDS-PAGE under reducing and non-reducing conditions as before. Shown in FIG. 9 is sucrose gradient analysis of surface expressed uncross-linked full length radiolabeled HeV G. Here it is observed that in the non-reduced fractions, >95% of the full-length HeV G exists as the apparent tetrameric species (FIG. 9A, lanes 2-5) and this oligomeric species is clearly dependent on disulfide bonds as illustrated by the corresponding reduced fractions which are monomeric (FIG. 9B, lanes 2-5). In addition, identical sucrose gradient profiles were seen regardless of whether cross-linking reagent was used or not indicating that the native cell-surface expressed G forms a very stable tetrameric oligomer. The protein's natural membrane anchor domain and or its cytoplasmic tail may contribute to this stability. Nevertheless, the majority (~60-70%) of the $sG_{S\text{-}tag}$ glycoprotein product produced here is an oligomeric dimer which indicates that it may retain important and useful native structural features.

Example 5

Inhibition of HeV and NiV Infection by Soluble HeV G

Figure 11:
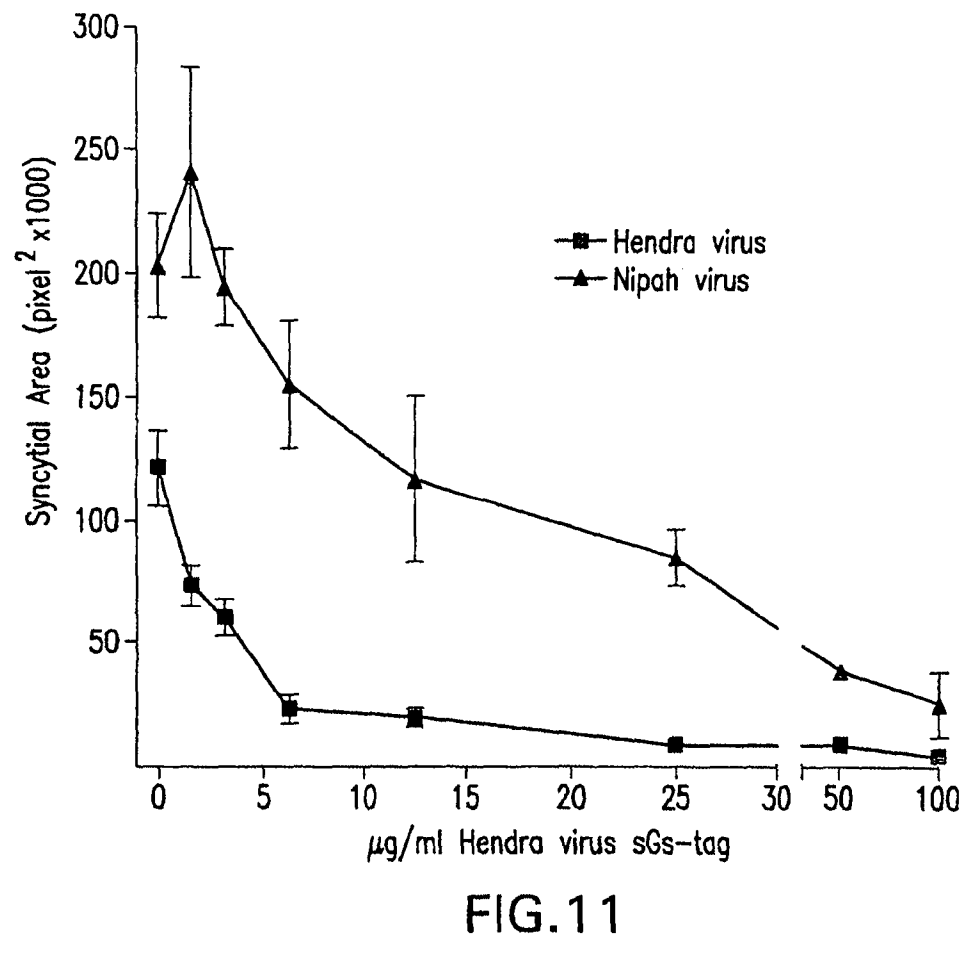

It was next evaluated if $sG_{S\text{-}tag}$ effects on live virus infection of Vero cells in culture. Here, following preincubation of Vero cells with various concentrations of $sG_{S\text{-}tag}$, the cells were infected with $1.5 \times 10^3$ $TCID_{50}$/ml and $7.5 \times 10^2$ $TCID_{50}$/ml of live HeV or NiV, respectively, in the presence of $sG_{S\text{-}tag}$ for 30 min, followed by removal of the virus inoculum and incubation with $sG_{S\text{-}tag}$. After 24 hrs in culture, the number of HeV and NiV infection foci was quantified by specific immunostaining of cell monolayers with an anti-phosphoprotein (P) as detailed in the methods. Representative examples of infected Vero cells in the presence or absence of $sG_{S\text{-}tag}$ are shown in FIG. 10. Typically, infection of Vero cells with live HeV or NiV produces characteristic syncytium morphologies for each virus. Immunofluorescence for HeV P protein in HeV syncytia demonstrated that HeV reproducibly infects and incorporates surrounding cells into each syncytium with cell nuclei and viral protein equally detectable throughout the majority of infected cells (FIG. 10A). NiV infected cells initially show a similar appearance to HeV syncytia, but ultimately incorporated nuclei within each giant cell are sequestered together towards the periphery while the remaining cellular debris is also arranged around the outside leaving the central region largely empty. Thus, immunofluorescence for HeV P protein in NiV syncytia often appear as hollow spheres coated in viral antigen (FIG. 10B) and by comparison, the untreated control HeV infections produce smaller syncytium relative to the untreated NiV control (FIGS. 10A and 10B). FIGS. 10C and 10D are representative examples of HeV and NiV-infected Vero cells in the presence of 100 μg/ml. $sG_{S\text{-}tag}$. Although there were still some infected cells present as detected by immunofluorescence, syncytia formation was completely blocked in both HeV and NiV-infected cells (FIGS. 10C and 10D, respectively). Furthermore, quantitative analysis of the inhibition of HeV and NiV infection by purified $sG_{S\text{-}tag}$ glycoprotein revealed a dose-dependent response, further demonstrating its specificity, as shown in FIG. 11. Together these data provide strong evidence that HeV and NiV utilize a common receptor on the surface of the host cell. Additionally, the specific inhibition of both viruses by $sG_{S\text{-}tag}$ further demonstrated that the $sG_{S\text{-}tag}$ construct maintains important native structural elements. Interestingly, HeV infection was inhibited significantly better than NiV such that the $IC_{50}$ determined for $sG_{S\text{-}tag}$ was four-fold greater for NiV (13.20 μg/ml) than for HeV (3.3 μg/ml) (FIG. 11). Given the current evidence suggesting both viruses utilize a common receptor, the reasons for the differences observed in $sG_{S\text{-}tag}$ inhibition of virus infection versus cell-fusion remain unknown. A similar difference in the ability of $sG_{S\text{-}tag}$ to inhibit HeV and NiV-mediated cell-fusion was not observed, as demonstrated in FIG. 3. Although HeV-mediated fusion was more potent than NiV-mediated fusion, illustrated by the higher levels of substrate turnover, the $sG_{S\text{-}tag}$ $IC_{50}$ in both cell-fusion assays remained constant. In previous reports, it has been demonstrated through heterotypic function that the difference in cell-fusion rates between HeV and NiV was dependent on the fusion protein. Here, it is demonstrated that natural NiV infection appears to be more vigorous than HeV infection. Perhaps other viral proteins present during infection are influencing the kinetics of infection thus altering the inhibition susceptibility, or they may be differences in the affinity of HeV sG versus NiV G to the cell surface expressed receptor.

Example 6

Soluble HeV G Elicits a Potent Virus-Neutralizing Polyclonal Antibody Response

With few exceptions, it is the envelope glycoproteins of viruses to which virtually all neutralizing antibodies are directed and all successful human viral vaccines induce neutralizing antibodies that can cross-react with immunologically relevant strains of a virus. More specifically, virus-neutralizing antibodies are the key vaccine-induced protective mechanism in the case of the paramyxoviruses mumps and measles, and it has been shown that vaccinia virus expressed full-length envelope glycoproteins from NiV can elicit virus-neutralizing antibodies. Data indicate that the $sG_{S\text{-}tag}$ glycoprotein retains important structural features based on its abilities to specifically bind receptor positive cells and block both HeV and NiV-mediated fusion and infection. Thus, the immunization of animals with sG should potentially generate potent virus-neutralizing antibodies. To test this possibility, purified sG$_{S-tag}$ was used to immunize rabbits and the resulting anti-G antiserum evaluated in virus neutralization assays with both HeV and NiV. Table 1 summarizes the neutralization of HeV and NiV infection by the polyclonal rabbit anti-G sera. The sera from both rabbits were capable of complete neutralization of HeV at a dilution of 1:1280. NiV was also neutralized by the sG$_{S-tag}$ antiserum, with complete neutralization at a dilution of 1:640. A two fold difference in titer is consistent with partial antibody cross-reactivity of the HeV and NiV G glycoproteins. Pre-bleeds from both rabbits were also tested for their ability to neutralize HeV and NiV. Although there was slight neutralization at the highest concentration, this activity was completely abrogated upon dilution of the sera. Previous studies have demonstrated that HeV and NiV antisera do cross neutralize, with each serum being slightly less effective against the heterotypic virus (14). Moreover, it has been demonstrated a similar trend in cross-neutralization using the cell-fusion assay for HeV and NiV (4,81). Because sG$_{S-tag}$ was able to elicit such a potent immune response with high levels of neutralizing antibodies, it may provide an avenue for vaccine development strategies.

Other embodiments and uses of the invention will be apparent to those skilled in the art from consideration of the specification and practice of the invention disclosed herein. All references cited herein, including all publications, U.S. and foreign patents and patent applications, are specifically and entirely incorporated by reference. It is intended that the specification and examples be considered exemplary only with the true scope and spirit of the invention indicated by the following claims.

CITED REFERENCES

1. Anonymous. 1999. From the Centers for Disease Control and Prevention. Outbreak of Hendra-like virus—Malaysia and Singapore, 1998-1999. Jama 281:1787-8.
2. Baker, K. A., R. E. Dutch, R. A. Lamb, and T. S. Jardetzky. 1999. Structural basis for paramyxovirus-mediated membrane fusion. Mol Cell 3:309-19.
3. Berger, E. A., P. M. Murphy, and J. M. Farber. 1999. Chemokine receptors as HIV-1 coreceptors: roles in viral entry, tropism, and disease. Annu Rev Immunol 17:657-700.
4. Bossart, K. N., L.-F. Wang, B. T. Eaton, and C. C. Broder. 2001. Functional expression and membrane fusion tropism of the envelope glycoproteins of Hendra virus. Virology 290:121-35.
5. Bossart, K. N., L. F. Wang, M. N. Flora, K. B. Chua, S. K. Lam, B. T. Eaton, and C. C. Broder. 2002. Membrane fusion tropism and heterotypic functional activities of the nipah virus and hendra virus envelope glycoproteins. J Virol 76:11186-98.
6. Broder, C. C., and P. L. Earl. 1999. Recombinant vaccinia viruses. Design, generation, and isolation. Mol Biotechnol 13:223-45.
7. Broder, C. C., P. L. Earl, D. Long, S. T. Abedon, B. Moss, and R. W. Doms. 1994. Antigenic implications of human immunodeficiency virus type 1 envelope quaternary structure: oligomer-specific and -sensitive monoclonal antibodies. Proc Natl Acad Sci USA 91:11699-703.
8. Chan, D. C., D. Fass, J. M. Berger, and P. S. Kim. 1997. Core structure of gp41 from the HIV envelope glycoprotein. Cell 89:263-73.
9. Chen, L., P. M. Colman, L. J. Cosgrove, M. C. Lawrence, L. 3. Lawrence, P. A. Tulloch, and J. J. Gorman. 2001. Cloning, expression, and crystallization of the fusion protein of Newcastle disease virus. Virology 290:290-9.
10. Chen, L., 3.3. Gorman, 3. McKimm-Breschkin, L. J. Lawrence, P. A. Tulloch, B. J. Smith, P. M. Colman, and M. C. Lawrence. 2001. The structure of the fusion glycoprotein of Newcastle disease virus suggests a novel paradigm for the molecular mechanism of membrane fusion. Structure (Camb) 9:255-66.
11. Chua, K. B., W. J. Bellini, P. A. Rota, B. H. Harcourt, A. Tamin, S. K. Lam, T. G. Ksiazek, P. E. Rollin, S. R. Zaki, W. Shieh, C. S. Goldsmith, D. J. Gubler, J. T. Roehrig, B. Eaton, A. R. Gould, J. Olson, H. Field, P. Daniels, A. E. Ling, C. J. Peters, L. J. Anderson, and B. W. Mahy. 2000. Nipah virus: a recently emergent deadly paramyxovirus. Science 288:1432-5.
12. Chua, K. B., K. J. Goh, K. T. Wong, A. Kamarulzaman, P. S. Tan, T. G. Ksiazek, S. R. Zaki, G. Paul, S. K. Lam, and C. T. Tan. 1999. Fatal encephalitis due to Nipah virus among pig-farmers in Malaysia [see comments]. Lancet 354:1257-9.
13. Citovsky, V., P. Yanai, and A. Loyter. 1986. The use of circular dichroism to study conformational changes induced in Sendai virus envelope glycoproteins. A correlation with the viral fusogenic activity. J Biol Chem 261:2235-9.
14. Crameri, G., L. F. Wang, C. Morrissy, J. White, and B. T. Eaton. 2002. A rapid immune plaque assay for the detection of Hendra and Nipah viruses and anti-virus antibodies. J Virol Methods 99:41-51.
15. Crennell, S., T. Takimoto, A. Portner, and G. Taylor. 2000. Crystal structure of the multifunctional paramyxovirus hemagglutinin-neuraminidase. Nat Struct Biol 7:1068-74.
16. Doms, R. W., R. Lamb, J. K. Rose, and A. Helenius. 1993. Folding and assembly of viral membrane proteins. Virology 193:545-562.
17. Doms, R. W., and J. P. Moore. 2000. HIV-1 membrane fusion. Targets Of opportunity. J Cell Biol 151:F9-F14.
18. Doms, R. W., and D. Trono. 2000. The plasma membrane as a combat zone in the HIV battlefield [In Process Citation]. Genes Dev 14:2677-88.
19. Dorig, R. E., A. Marcil, A. Chopra, and C. D. Richardson. 1993. The human CD46 molecule is a receptor for measles virus (Edmonston strain). Cell 75:295-305.
20. Dutch, R. E., R. N. Hagglund, M. A. Nagel, R. G. Paterson, and R. A. Lamb. 2001. *Paramyxovirus* fusion (F) protein: a conformational change on cleavage activation. Virology 281:138-50.
21. Fass, D., S. C. Harrison, and P. S. Kim. 1996. Retrovirus envelope domain at 1.7 angstrom resolution. Nat Struct Biol 3:465-9.
22. Field, H., P. Young, J. M. Yob, J. Mills, L. Hall, and J. Mackenzie. 2001. The natural history of Hendra and Nipah viruses. Microbes Infect 3:307-14.
23. Goh, K. J., C. T. Tan, N. K. Chew, P. S. Tan, A. Kamarulzaman, S. A. Sarji, K. T. Wong, B. J. Abdullah, K. B. Chua, and S. K. Lam. 2000. Clinical features of Nipah virus encephalitis among pig farmers in Malaysia [see comments]. N Engl J Med 342:1229-35.
24. Halpin, K., P. L. Young, H. Field, and J. S. Mackenzie. 1999. Newly discovered viruses of flying foxes. Vet Microbiol 68:83-7.
25. Halpin, K., P. L. Young, H. E. Field, and J. S. Mackenzie. 2000. Isolation of Hendra virus from pteropid bats: a natural reservoir of Hendra virus. J Gen Virol 81:1927-1932.
26. Hernandez, L. D., L. R. Hoffman, T. G. Wolfsberg, and J. M. White. 1996. Virus-cell and cell-cell fusion. Annu Rev Cell Dev Biol 12:627-61.

27. Hooper, P., S. Zaki, P. Daniels, and D. Middleton. 2001. Comparative pathology of the diseases caused by Hendra and Nipah viruses. Microbes Infect 3:315-22.
28. Hooper, P. T., H. A. Westbury, and G. M. Russell. 1997. The lesions of experimental equine morbillivirus disease in cats and guinea pigs. Vet Pathol 34:323-9.
29. Hughson, F. M. 1997. Enveloped viruses: a common mode of membrane fusion? Curr Biol 7:R565-9.
30. Hunter, E. 1997. Viral entry and receptors, p. 71-119. In S. H. Coffin, S. H. Hughes, and H. E. Varmus (ed.), Retroviruses. Cold Spring Harbor Laboratory Press, New York.
31. Hurtley, S. M., and A. Helenius. 1989. Protein oligomerization in the endoplasmic reticulum. Ann. Rev. Cell Biol. 5:277-307.
32. Jiang, S., K. Lin, N. Strick, and A. R. Neurath. 1993. HIV-1 inhibition by a peptide. Nature 365:113.
33. Joshi, S. B., R. E. Dutch, and R. A. Lamb. 1998. A core trimer of the paramyxovirus fusion protein: parallels to influenza virus hemagglutinin and HIV-1 gp41. Virology 248:20-34.
34. Klenk, H. D., and W. Garten. 1994. Host cell proteases controlling virus pathogenicity. Trends Microbiol 2:39-43.
35. Lamb, R. A. 1993. *Paramyxovirus* fusion: A hypothesis for changes. Virology 197:1-11.
36. Lamb, R. A., and D. Kolakofsky. 2001. Paramyxoviridae: The viruses and their replication., p. 1305-1340. In D. M. Knipe and P. M. Howley (ed.), Fields Virology, 4 ed. Lippincott Williams & Wilkins, Philadelphia.
37. Lambert, D. M., S. Barney, A. L. Lambert, K. Guthrie, R. Medinas, D. E. Davis, T. Bucy, J. Erickson, G. Merutka, and S. R. Petteway, Jr. 1996. Peptides from conserved regions of paramyxovirus fusion (F) proteins are potent inhibitors of viral fusion. Proc Natl Acad Sci USA 93:2186-91.
38. Lee, K. E., T. Umapathi, C. B. Tan, H. T. Tjia, T. S. Chua, H. M. Oh, K. M. Fock, A. Kurup, A. Das, A. K. Tan, and W. L. Lee. 1999. The neurological manifestations of Nipah virus encephalitis, a novel paramyxovirus. Ann Neurol 46:428-32.
39. Lim, C. C., Y. Y. Sitoh, F. Hui, K. E. Lee, B. S. Ang, E. Lim, W. E. Lim, H. M. Oh, P. A. Tambyah, J. S. Wong, C. B. Tan, and T. S. Chee. 2000. Nipah viral encephalitis or Japanese encephalitis? MR findings in a new zoonotic disease. AJNR Am J Neuroradiol 21:455-61.
40. Markwell, M. A., and C. F. Fox. 1980. Protein-protein interactions within paramyxoviruses identified by native disulfide bonding or reversible chemical cross-linking. J Virol 33:152-66.
41. McGinnes, L. W., K. Gravel, and T. G. Morrison. 2002. Newcastle disease virus HN protein alters the conformation of the F protein at cell surfaces. J Virol 76:12622-33.
42. Middleton, D. J., H. A. Westbury, C. J. Morrissy, B. M. van der Heide, G. M. Russell, M. A. Braun, and A. D. Hyatt. 2002. Experimental nipah virus infection in pigs and cats. J Comp Pathol 126:124-36.
43. Morrison, T. G. 1988. Structure, function, and intracellular processing of paramyxovirus membrane proteins. Virus Res 10:113-35.
44. Morrison, T. G. 2001. The three faces of paramyxovirus attachment proteins. Trends Microbiol 9:103-5.
45. Mounts, A. W., H. Kaur, U. D. Parashar, T. G. Ksiazek, D. Cannon, J. T. Arokiasamy, L. J. Anderson, and M. S. Lye. 2001. A cohort study of health care workers to assess nosocomial transmissibility of Nipah virus, Malaysia, 1999. J Infect Dis 183:810-3.
46. Murray, K., P. Selleck, P. Hooper, A. Hyatt, A. Gould, L. Gleeson, H. Westbury, L. Hiley, L. Selvey, B. Rodwell, and et al. 1995. A morbillivirus that caused fatal disease in horses and humans. Science 268:94-7.
47. Naniche, D., G. Varior-Krishnan, F. Cervoni, T. F. Wild, B. Rossi, C. Rabourdin-Combe, and D. Gerlier. 1993. Human membrane cofactor protein (CD46) acts as a cellular receptor for measles virus. J Virol 67:6025-32.
48. Nussbaum, O., C. C. Broder, B. Moss, L. B. Stem, S. Rozenblatt, and E. A. Berger. 1995. Functional and structural interactions between measles virus hemagglutinin and CD46. J Virol 69:3341-9.
49. O'Sullivan, J. D., A. M. Allworth, D. L. Paterson, T. M. Snow, R. Boots, L. J. Gleeson, A. R. Gould, A. D. Hyatt, and J. Bradfield. 1997. Fatal encephalitis due to novel paramyxovirus transmitted from horses. Lancet 349:93-5.
50. Paterson, R. G., M. L. Johnson, and R. A. Lamb. 1997. *Paramyxovirus* fusion (F) protein and hemagglutinin-neuraminidase (HN) protein interactions: intracellular retention of F and HN does not affect transport of the homotypic HN or F protein. Virology 237:1-9.
51. Plemper, R. K., A. L. Hammond, and R. Cattaneo. 2001. Measles virus envelope glycoproteins hetero-oligomerize in the endoplasmic reticulum. J Biol Chem 276:44239-46.
52. Rapaport, D., M. Ovadia, and Y. Shai. 1995. A synthetic peptide corresponding to a conserved heptad repeat domain is a potent inhibitor of Sendai virus-cell fusion: an emerging similarity with functional domains of other viruses. Embo J 14:5524-31.
53. Russell, C. J., T. S. Jardetzky, and R. A. Lamb. 2001. Membrane fusion machines of paramyxoviruses: capture of intermediates of fusion. Embo J 20:4024-34.
54. Russell, R., R. G. Paterson, and R. A. Lamb. 1994. Studies with cross-linking reagents on the oligomeric form of the paramyxovirus fusion protein. Virology 199:160-8.
55. Scheid, A., and P. W. Choppin. 1974. Identification of biological activities of paramyxovirus glycoproteins. Activation of cell fusion, hemolysis, and infectivity of proteolytic cleavage of an inactive precursor protein of Sendai virus. Virology 57:475-90.
56. Singh, M., B. Berger, and P. S. Kim. 1999. LearnCoil-VMF: computational evidence for coiled-coil-like motifs in many viral membrane-fusion proteins. J Mol Biol 290:1031-41.
57. Stone-Hulslander, J., and T. G. Morrison. 1997. Detection of an interaction between the HN and F proteins in Newcastle disease virus-infected cells. J Virol 71:6287-95.
58. Takimoto, T., G. L. Taylor, H. C. Connaris, S. 3. Crennell, and A. Portner. 2002. Role of the hemagglutinin-neuraminidase protein in the mechanism of paramyxovirus-cell membrane fusion. J Virol 76:13028-33.
59. Takimoto, T., G. L. Taylor, S. J. Crennell, R. A. Scroggs, and A. Portner. 2000. Crystallization of Newcastle disease virus hemagglutinin-neuraminidase glycoprotein. Virology 270:208-14.
60. Tan, C. T., and K. S. Tan. 2001. Nosocomial transmissibility of Nipah virus. J Infect Dis 184:1367.
61. Tatsuo, H., N. Ono, K. Tanaka, and Y. Yanagi. 2000. SLAM (CDw150) is a cellular receptor for measles virus. Nature 406:893-7.
62. Tatsuo, H., N. Ono, and Y. Yanagi. 2001. Morbilliviruses use signaling lymphocyte activation molecules (CD150) as cellular receptors. I Virol 75:5842-50.
63. Wang, L., B. H. Harcourt, M. Yu, A. Tamin, P. A. Rota, W. J. Bellini, and B. T. Eaton. 2001. Molecular biology of Hendra and Nipah viruses. Microbes Infect 3:279-87.
64. Wang, L. F., W. P. Michalski, M. Yu, L. I. Pritchard, G. Crameri, B. Shiell, and B. T. Eaton. 1998. A novel P/V/C gene in a new member of the Paramyxoviridae family, which causes lethal infection in humans, horses, and other animals. J Virol 72:1482-90.
65. Westbury, H. A., P. T. Hooper, S. L. Brouwer, and P. W. Selleck. 1996. Susceptibility of cats to equine morbillivirus. Aust Vet J 74:132-4.
66. Westbury, H. A., P. T. Hooper, P. W. Selleck, and P. K. Murray. 1995. Equine morbillivirus pneumonia: susceptibility of laboratory animals to the virus. Aust Vet J 72:278-9.
67. Wild, C. T., D. C. Shugars, T. K. Greenwell, C. B. McDanal, and T. J. Matthews. 1994. Peptides corresponding to a predictive alpha-helical domain of human immunodeficiency virus type 1 gp41 are potent inhibitors of virus infection. Proc Natl Acad Sci USA 91:9770-4.
68. Wild, T. F., and R. Buckland. 1997. Inhibition of measles virus infection and fusion with peptides corresponding to the leucine zipper region of the fusion protein. J Gen Virol 78:107-11.
69. Wiley, D. C., and J. J. Skehel. 1987. The structure and function of the hemagglutinin membrane glycoprotein of influenza virus. Ann. Rev. Biochem. 56:365-394.
70. Williamson, M. M., P. T. Hooper, P. W. Selleck, L. J. Gleeson, P. W. Daniels, H. A. Westbury, and P. K. Murray. 1998. Transmission studies of Hendra virus (equine morbillivirus) in fruit bats, horses and cats. Aust Vet J 76:813-8.
71. Wilson, I. A., J. J. Skehel, and D. C., Wiley. 1981. Structure of the haemagglutinin membrane glycoprotein of influenza virus at 3 A resolution. Nature 289:366-73.
72. Wong, S. C., M. H. Ooi, M. N. Wong, P. H. Tio, T. Solomon, and M. J. Cardosa. 2001. Late presentation of Nipah virus encephalitis and kinetics of the humoral immune response. J Neurol Neurosurg Psychiatry 71:552-4.
73. Yao, Q., X. Hu, and R. W. Compans. 1997. Association of the parainfluenza virus fusion and hemagglutinin-neuraminidase glycoproteins on cell surfaces. J Virol 71:650-6.
74. Young, J. K., R. P. Hicks, G. E. Wright, and T. G. Morrison. 1997. Analysis of a peptide inhibitor of paramyxovirus (NDV) fusion using biological assays, NMR, and molecular modeling. Virology 238:291-304.
75. Young, J. K., D. Li, M. C. Abramowitz, and T. G. Morrison. 1999. Interaction of peptides with sequences from the Newcastle disease virus fusion protein heptad repeat regions. J Virol 73:5945-56.
76. Young, P. L., K. Halpin, P. W. Selleck, H. Field, J. L. Gravel, M. A. Kelly, and J. S. Mackenzie. 1996. Serologic evidence for the presence in Pteropus bats of a paramyxovirus related to equine morbillivirus. Emerg Infect Dis 2:239-40.
77. Yu, M., E. Hansson, J. P. Langedijk, B. T. Eaton, and L. F. Wang. 1998. The attachment protein of Hendra virus has high structural similarity but limited primary sequence homology compared with viruses in the genus *Paramyxovirus*. Virology 251:227-33.
78. Yu, M., E. Hansson, B. Shiell, W. Michalski, B. T. Eaton, and L. F. Wang. 1998. Sequence analysis of the Hendra virus nucleoprotein gene: comparison with other members of the subfamily Paramyxovirinae. J Gen Virol 79:1775-80.
79. Zhao, X., M. Singh, V. N. Malashkevich, and P. S. Kim. 2000. Structural characterization of the human respiratory syncytial virus fusion protein core. Proc Natl Acad Sci USA 97:14172-7.
80. Zhu, J., C. W. Zhang, Y. Qi, P. Tien, and G. F. Gao. 2002. The fusion protein core of measles virus forms stable coiled-coil trimer. Biochem Biophys Res Commun 299:897-902.
81. Bossart, K. N., and C. C. Broder. 2004. Viral glycoprotein-mediated cell fusion assays using vaccinia virus vectors. Methods Mol. Biol. 269:309-332.

TABLE 1

| Dilution | HeV | | NiV | |
| --- | --- | --- | --- | --- |
| | Rabbit 405 | Rabbit 406 | Rabbit 405 | Rabbit 406 |
| 1:10 | -- | -- | -- | -- |
| 1:20 | -- | -- | -- | -- |
| 1:40 | -- | -- | -- | -- |
| 1:80 | -- | -- | -- | -- |
| 1:160 | -- | -- | -- | -- |
| 1:320 | -- | -- | -- | -- |
| 1:640 | -- | -- | -- | -- |
| 1:1,280 | -- | -- | ++ | -+ |
| 1:2,560 | -- | -+ | ++ | ++ |
| 1:5,120 | -- | ++ | ++ | ++ |
| 1:10,240 | ++ | ++ | ++ | ++ |
| 1:20,480 | ++ | ++ | ++ | ++ |

The invention claimed is:

1. A method of preventing infection by a Nipah virus in a subject comprising administering to said subject a composition comprising an isolated oligomeric peptide wherein the monomers of the oligomeric peptide consist of the ectodomain of the Hendra virus G protein with an amino acid sequence of SEQ ID NO: 16 or a sequence at least 90% identical to SEQ ID NO: 16.

2. The method of claim 1, wherein the isolated oligomeric peptide retains one or more characteristics of a native Hendra virus G protein.

3. The method of claim 1, wherein the oligomeric peptide is linked to another peptide.

4. The method of claim 3, wherein the another peptide is derived from vaccinia virus.

5. The method of claim 1, wherein the oligomeric peptide is a dimer.

6. The method of claim 1, wherein the oligomeric peptide is a tetramer.

7. The method of claim 1, wherein the composition further comprises an adjuvant.

* * * * *

SEQUENCE LISTING

<160> NUMBER OF SEQ ID NOS: 17

<210> SEQ ID NO 1
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
gtcgaccacc atgcaaaatt acaccagaac gactgataat                           40

<210> SEQ ID NO 2
<211> LENGTH: 45
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 2
gtttaaacgt cgaccaatca actctctgaa cattgggcag gtatc                    45

<210> SEQ ID NO 3
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
ctcgagcacc atgcaaaatt acacaagatc aacagacaa                           39

<210> SEQ ID NO 4
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
ctcgagtagc agccggatca agcttatgta cattgctctg gtatc                    45

<210> SEQ ID NO 5
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
caaggagacc gctgctgcta agttcgaacg ccagcacatg gattct                   46

<210> SEQ ID NO 6
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
aattagaatc catgtgctgg cgttcgaact tagcagcagc ggtctccttg gtac          54

<210> SEQ ID NO 7
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
cgaacaaaag ctcatctcag aagaggatct g                                   31

<210> SEQ ID NO 8
<211> LENGTH: 39
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 8
aattcagatc ctcttctgag atgagctttt gttcggtac                            39

<210> SEQ ID NO 9
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
tcgacccacc atggagacag acacactcct gcta                                 34

<210> SEQ ID NO 10
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Met Glu Thr Asp Thr Leu Leu Leu Trp Val Leu Leu Leu Trp Val Pro
 1               5                  10                  15

Gly Ser Thr Gly Asp
            20

<210> SEQ ID NO 11
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Ala Ala Gln Pro Ala Arg Arg Ala Arg Arg Thr Lys Leu Gly Thr
 1               5                  10                  15

<210> SEQ ID NO 12
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Lys Glu Thr Ala Ala Ala Lys Phe Glu Arg Gln His Met Asp Ser
 1               5                  10                  15

<210> SEQ ID NO 13
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Glu Gln Lys Leu Ile Ser Glu Glu Asp Leu
 1               5                  10
```

-continued

<210> SEQ ID NO 14
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Asn Ser Ala Asp Ile Gln His Ser Gly Gly Arg Ser Thr Thr Met
 1               5                  10                  15

<210> SEQ ID NO 15
<211> LENGTH: 421
<212> TYPE: PRT
<213> ORGANISM: Hendra virus

<400> SEQUENCE: 15

Gly Leu Pro Asn Gln Ile Cys Leu Gln Lys Thr Thr Ser Thr Ile Leu
 1               5                  10                  15

Lys Pro Arg Leu Ile Ser Tyr Thr Leu Pro Ile Asn Arg Glu Gly Val
            20                  25                  30

Cys Ile Thr Asp Pro Leu Leu Ala Val Asp Asn Gly Phe Phe Ala Tyr
        35                  40                  45

Ser His Leu Glu Lys Ile Gly Ser Cys Thr Arg Gly Ile Ala Lys Gln
    50                  55                  60

Arg Ile Ile Gly Val Gly Glu Val Leu Asp Arg Gly Asp Lys Val Pro
65                  70                  75                  80

Ser Met Phe Met Thr Asn Val Trp Thr Pro Pro Asn Pro Ser Thr Ile
                85                  90                  95

His His Cys Ser Ser Thr Tyr His Glu Asp Phe Tyr Tyr Thr Leu Cys
            100                 105                 110

Ala Val Ser His Val Gly Asp Pro Ile Leu Asn Ser Thr Ser Trp Thr
        115                 120                 125

Glu Ser Leu Ser Leu Ile Arg Leu Ala Val Arg Pro Lys Ser Asp Ser
    130                 135                 140

Gly Asp Tyr Asn Gln Lys Tyr Ile Ala Ile Thr Lys Val Glu Arg Gly
145                 150                 155                 160

Lys Tyr Asp Lys Val Met Pro Tyr Gly Pro Ser Gly Ile Lys Gln Gly
                165                 170                 175

Asp Thr Leu Tyr Phe Pro Ala Val Gly Phe Leu Pro Arg Thr Glu Phe
            180                 185                 190

Gln Tyr Asn Asp Ser Asn Cys Pro Ile Ile His Cys Lys Tyr Ser Lys
        195                 200                 205

Ala Glu Asn Cys Arg Leu Ser Met Gly Val Asn Ser Lys Ser His Tyr
    210                 215                 220

Ile Leu Arg Ser Gly Leu Leu Lys Tyr Asn Leu Ser Leu Gly Gly Asp
225                 230                 235                 240

Ile Ile Leu Gln Phe Ile Glu Ile Ala Asp Asn Arg Leu Thr Ile Gly
                245                 250                 255

Ser Pro Ser Lys Ile Tyr Asn Ser Leu Gly Gln Pro Val Phe Tyr Gln
            260                 265                 270

Ala Ser Tyr Ser Trp Asp Thr Met Ile Lys Leu Gly Asp Val Asp Thr
        275                 280                 285

Val Asp Pro Leu Arg Val Gln Trp Arg Asn Asn Ser Val Ile Ser Arg
    290                 295                 300

```
Pro Gly Gln Ser Gln Cys Pro Arg Phe Asn Val Cys Pro Glu Val Cys
305                 310                 315                 320

Trp Glu Gly Thr Tyr Asn Asp Ala Phe Leu Ile Asp Arg Leu Asn Trp
            325                 330                 335

Val Ser Ala Gly Val Tyr Leu Asn Ser Asn Gln Thr Ala Glu Asn Pro
            340                 345                 350

Val Phe Ala Val Phe Lys Asp Asn Glu Ile Leu Tyr Gln Val Pro Leu
            355                 360                 365

Ala Glu Asp Asp Thr Asn Ala Gln Lys Thr Ile Thr Asp Cys Phe Leu
            370                 375                 380

Leu Glu Asn Val Ile Trp Cys Ile Ser Leu Val Glu Ile Tyr Asp Thr
385                 390                 395                 400

Gly Asp Ser Val Ile Arg Pro Lys Leu Phe Ala Val Lys Ile Pro Ala
            405                 410                 415

Gln Cys Ser Glu Ser
            420

<210> SEQ ID NO 16
<211> LENGTH: 534
<212> TYPE: PRT
<213> ORGANISM: Hendra virus

<400> SEQUENCE: 16

Gln Asn Tyr Thr Arg Thr Thr Asp Asn Gln Ala Leu Ile Lys Glu Ser
1               5                   10                  15

Leu Gln Ser Val Gln Gln Gln Ile Lys Ala Leu Thr Asp Lys Ile Gly
            20                  25                  30

Thr Glu Ile Gly Pro Lys Val Ser Leu Ile Asp Thr Ser Ser Thr Ile
            35                  40                  45

Thr Ile Pro Ala Asn Ile Gly Leu Leu Gly Ser Lys Ile Ser Gln Ser
        50                  55                  60

Thr Ser Ser Ile Asn Glu Asn Val Asn Asp Lys Cys Lys Phe Thr Leu
65              70                  75                  80

Pro Pro Leu Lys Ile His Glu Cys Asn Ile Ser Cys Pro Asn Pro Leu
                85                  90                  95

Pro Phe Arg Glu Tyr Arg Pro Ile Ser Gln Gly Val Ser Asp Leu Val
            100                 105                 110

Gly Leu Pro Asn Gln Ile Cys Leu Gln Lys Thr Thr Ser Thr Ile Leu
        115                 120                 125

Lys Pro Arg Leu Ile Ser Tyr Thr Leu Pro Ile Asn Thr Arg Glu Gly
130                 135                 140

Val Cys Ile Thr Asp Pro Leu Leu Ala Val Asp Asn Gly Phe Phe Ala
145                 150                 155                 160

Tyr Ser His Leu Glu Lys Ile Gly Ser Cys Thr Arg Gly Ile Ala Lys
                165                 170                 175

Gln Arg Ile Ile Gly Val Gly Glu Val Leu Asp Arg Gly Asp Lys Val
            180                 185                 190

Pro Ser Met Phe Met Thr Asn Val Trp Thr Pro Pro Asn Pro Ser Thr
        195                 200                 205

Ile His His Cys Ser Ser Thr Tyr His Glu Asp Phe Tyr Tyr Thr Leu
    210                 215                 220

Cys Ala Val Ser His Val Gly Asp Pro Ile Leu Asn Ser Thr Ser Trp
225                 230                 235                 240

Thr Glu Ser Leu Ser Leu Ile Arg Leu Ala Val Arg Pro Lys Ser Asp
                245                 250                 255
```

-continued

```
Ser Gly Asp Tyr Asn Gln Lys Tyr Ile Ala Ile Thr Lys Val Glu Arg
            260                 265                 270

Gly Lys Tyr Asp Lys Val Met Pro Tyr Gly Pro Ser Gly Ile Lys Gln
        275                 280                 285

Gly Asp Thr Leu Tyr Phe Pro Ala Val Gly Phe Leu Pro Arg Thr Glu
        290                 295                 300

Phe Gln Tyr Asn Asp Ser Asn Cys Pro Ile Ile His Cys Lys Tyr Ser
305                 310                 315                 320

Lys Ala Glu Asn Cys Arg Leu Ser Met Gly Val Asn Ser Lys Ser His
                325                 330                 335

Tyr Ile Leu Arg Ser Gly Leu Leu Lys Tyr Asn Leu Ser Leu Gly Gly
            340                 345                 350

Asp Ile Ile Leu Gln Phe Ile Glu Ile Ala Asp Asn Arg Leu Thr Ile
        355                 360                 365

Gly Ser Pro Ser Lys Ile Tyr Asn Ser Leu Gly Gln Pro Val Phe Tyr
        370                 375                 380

Gln Ala Ser Tyr Ser Trp Asp Thr Met Ile Lys Leu Gly Asp Val Asp
385                 390                 395                 400

Thr Val Asp Pro Leu Arg Val Gln Trp Arg Asn Asn Ser Val Ile Ser
                405                 410                 415

Arg Pro Gly Gln Ser Gln Cys Pro Arg Phe Asn Val Cys Pro Glu Val
            420                 425                 430

Cys Trp Glu Gly Thr Tyr Asn Asp Ala Phe Leu Ile Asp Arg Leu Asn
        435                 440                 445

Trp Val Ser Ala Gly Val Tyr Leu Asn Ser Asn Gln Thr Ala Glu Asn
    450                 455                 460

Pro Val Phe Ala Val Phe Lys Asp Asn Glu Ile Leu Tyr Gln Val Pro
465                 470                 475                 480

Leu Ala Glu Asp Asp Thr Asn Ala Gln Lys Thr Ile Thr Asp Cys Phe
                485                 490                 495

Leu Leu Glu Asn Val Ile Trp Cys Ile Ser Leu Val Glu Ile Tyr Asp
            500                 505                 510

Thr Gly Asp Ser Val Ile Arg Pro Lys Leu Phe Ala Val Lys Ile Pro
        515                 520                 525

Ala Gln Cys Ser Glu Ser
        530

<210> SEQ ID NO 17
<211> LENGTH: 532
<212> TYPE: PRT
<213> ORGANISM: Nipah virus

<400> SEQUENCE: 17

Gln Asn Tyr Thr Arg Ser Thr Asp Asn Gln Ala Val Ile Lys Asp Ala
1               5                   10                  15

Leu Gln Gly Ile Gln Gln Gln Ile Lys Gly Leu Ala Asp Lys Ile Gly
            20                  25                  30

Thr Glu Ile Gly Pro Lys Val Ser Leu Ile Asp Thr Ser Ser Thr Ile
        35                  40                  45

Thr Ile Pro Ala Asn Ile Gly Leu Leu Gly Ser Lys Ile Ser Gln Ser
        50                  55                  60

Thr Ala Ser Ile Asn Glu Asn Val Asn Glu Lys Cys Lys Phe Thr Leu
65                  70                  75                  80

Pro Pro Leu Lys Ile His Glu Cys Asn Ile Ser Cys Pro Asn Pro Leu
                85                  90                  95
```

-continued

```
Pro Phe Arg Glu Tyr Arg Pro Gln Thr Glu Gly Val Ser Asn Leu Val
            100                 105                 110
Gly Leu Pro Asn Asn Ile Cys Leu Gln Lys Thr Ser Asn Gln Ile Leu
        115                 120                 125
Lys Pro Lys Leu Ile Ser Tyr Thr Leu Pro Val Val Gly Gln Ser Gly
    130                 135                 140
Thr Cys Ile Thr Asp Pro Leu Leu Ala Met Asp Glu Gly Tyr Phe Ala
145                 150                 155                 160
Tyr Ser His Leu Glu Arg Ile Gly Ser Cys Ser Arg Gly Val Ser Lys
                165                 170                 175
Gln Arg Ile Ile Gly Val Gly Glu Val Leu Asp Arg Gly Asp Glu Val
            180                 185                 190
Pro Ser Leu Phe Met Thr Asn Val Trp Thr Pro Pro Asn Pro Asn Thr
        195                 200                 205
Val Tyr His Cys Ser Ala Val Tyr Asn Asn Glu Phe Tyr Tyr Val Leu
    210                 215                 220
Cys Ala Val Ser Thr Val Gly Asp Pro Ile Leu Asn Ser Thr Tyr Trp
225                 230                 235                 240
Ser Gly Ser Leu Met Met Thr Arg Leu Ala Val Lys Pro Lys Ser Asn
                245                 250                 255
Gly Gly Gly Tyr Asn Gln His Gln Leu Ala Leu Arg Ser Ile Glu Lys
            260                 265                 270
Gly Arg Tyr Asp Lys Val Met Pro Tyr Gly Pro Ser Gly Ile Lys Gln
        275                 280                 285
Gly Asp Thr Leu Tyr Phe Pro Ala Val Gly Phe Leu Val Arg Thr Glu
    290                 295                 300
Phe Lys Tyr Asn Asp Ser Asn Cys Pro Ile Thr Lys Cys Gln Tyr Ser
305                 310                 315                 320
Lys Pro Glu Asn Cys Arg Leu Ser Met Gly Ile Arg Pro Asn Ser His
                325                 330                 335
Tyr Ile Leu Arg Ser Gly Leu Leu Lys Tyr Asn Leu Ser Asp Gly Glu
            340                 345                 350
Asn Pro Lys Val Val Phe Ile Glu Ile Ser Asp Gln Arg Leu Ser Ile
        355                 360                 365
Gly Ser Pro Ser Lys Ile Tyr Asp Ser Leu Gly Gln Pro Val Phe Tyr
    370                 375                 380
Gln Ala Ser Phe Ser Trp Asp Thr Met Ile Lys Phe Gly Asp Val Leu
385                 390                 395                 400
Thr Val Asn Pro Leu Val Val Asn Trp Arg Asn Asn Thr Val Ile Ser
                405                 410                 415
Arg Pro Gly Gln Ser Gln Cys Pro Arg Phe Asn Thr Cys Pro Glu Ile
            420                 425                 430
Cys Trp Glu Gly Val Tyr Asn Asp Ala Phe Leu Ile Asp Arg Ile Asn
        435                 440                 445
Trp Ile Ser Ala Gly Val Phe Leu Asp Ser Asn Gln Thr Ala Glu Asn
    450                 455                 460
Pro Val Phe Thr Val Phe Lys Asp Asn Glu Ile Leu Tyr Arg Ala Gln
465                 470                 475                 480
Leu Ala Ser Glu Asp Thr Asn Ala Gln Lys Thr Ile Thr Asn Cys Phe
                485                 490                 495
Leu Leu Lys Asn Lys Ile Trp Cys Ile Ser Leu Val Glu Ile Tyr Asp
            500                 505                 510
```

```
Thr Gly Asp Asn Val Ile Arg Pro Lys Leu Phe Ala Val Lys Ile Pro
        515                 520                 525

Glu Gln Cys Thr
    530
```